(12) United States Patent
Wensbo et al.

(10) Patent No.: US 7,576,077 B2
(45) Date of Patent: Aug. 18, 2009

(54) FUSED HETEROCYCLIC COMPOUNDS AND THEIR USE AS METABOTROPIC GLUTAMATE RECEPTOR ANTAGONISTS

(75) Inventors: David Wensbo, Södertälje (SE); Martin Johansson, Södertälje (SE); Alexander Minidis, Södertälje (SE); Karin Staaf, Södertälje (SE); Annika Kers, Södertälje (SE); Louise Edwards, Mississauga (CA); Methvin Isaac, Mississauga (CA); Tom Stefanac, Mississauga (CA); Abdelmalik Slassi, Mississauga (CA); Don McLeod, Salt Lake City, UT (US); Tao Xin, Mississauga (CA)

(73) Assignee: Astrazeneca AB, Sodertalje (SE)

( * ) Notice: Subject to any disclaimer, the term of this patent is extended or adjusted under 35 U.S.C. 154(b) by 465 days.

(21) Appl. No.: 11/060,560

(22) Filed: Feb. 18, 2005

(65) Prior Publication Data

US 2006/0009443 A1    Jan. 12, 2006

Related U.S. Application Data

(60) Provisional application No. 60/545,580, filed on Feb. 19, 2004.

(51) Int. Cl.
*A61P 25/00* (2006.01)
*C07D 487/02* (2006.01)
*A61K 31/55* (2006.01)

(52) U.S. Cl. ................................ 514/221; 540/568

(58) Field of Classification Search .............. 514/221; 540/568
See application file for complete search history.

(56) References Cited

FOREIGN PATENT DOCUMENTS

| WO | WO 01/12627 A1 | 2/2001 |
|---|---|---|
| WO | WO 03/029210 | 4/2003 |
| WO | WO 03/053922 | 7/2003 |
| WO | WO 03/077918 | 9/2003 |
| WO | WO 2004/014370 | 2/2004 |
| WO | WO 2004/014881 | 2/2004 |
| WO | WO 2004/014902 A2 | 2/2004 |
| WO | WO 2005/077345 | 8/2005 |
| WO | WO 2005/080356 | 9/2005 |

OTHER PUBLICATIONS

Aiba et al., "Reduced Hippocampal Long-term Potentiation and Context-Specific Deficit in Associative Learning in mGluR1 Mutant Mice", Cell vol. 79, p. 365- (1994).
Aiba et al., "Deficient Cerebellar Long-Term Depression and Impaired Motor Learning in mGluR1 Mutant Mice", Cell vol. 79, p. 377- (1994).
Baskys, "Metabotropic receptors and "slow" excitatory actions of glutamate agonists in the hippocampus", Trends in Neuroscience, vol. 15, p. 92- (1992).
Bashir et al., "zInduction of LTP in the hippcampus needs synaptic activation of glutamate metabotropic receptors", Nature, vol. 363, p. 347- (1993).
Bordi and Ugolini, "Group I Metabotropic Glutamate Receptors: Implications for Brain Diseases", Prog. Neurobiol. vol. 59, p. 55-79 (1999).
Bordi and Ugolini, "Involvement of mGluR$_5$ on acute nociceptive transmission", Brain Res. vol. 871, p. 223-233 (1999).
Bortolotto et al., "A molecular switch activated by metabotropic glutamate receptors regulates induction of long-term potentiation", Nature, vol. 368, p. 740- (1994).
Cunningham et al., "Excitatory Amino Acid Receptors: A gallery of new targets for Pharmacological Intervention", Life Sci. vol. 54, p. 135-148 (1994).
Gasparini et al, "Allosteric modulators of group I metabotropic glutamate receptors: novel subtype-selective ligands and therapeutics perspectives", Curr. Opin. Pharmacol. vol. 2, p. 43-49 (2002).
Hollman et al, "Cloned Glutamate Receptors", Ann. Rev. Neurosci. vol. 17, p. 31- (1994).
Holloway et al., "Lower Esophageal Sphincter Dysfunction in Gastroesphageal Reflux Disease", Gastroenterol. Clin. N. Amer. vol. 19, p. 517-535 (1990).
Joly et al., "Molecular, Functional, and Pharmacological characterization of the Metabotropic Glutamate Receptor Type 5 Splice Variants: Comparison with mGluR1", J. Neurosci. vol. 15, p. 3970-3981 (1995).
Knopfel et al., "Metabotropic Glutamate Receptors: Novel Targets for Drug Development", J. Med. Chem. vol. 38, p. 1417-1426 (1995).
Meller et al., "Acute mechanical hyperalgesia is produced by coactivation of AMPA and Metabotropic glutamate receptors", Neuroreport vol. 4, p. 879- (1993).

(Continued)

*Primary Examiner*—Brenda L Coleman
(74) *Attorney, Agent, or Firm*—Birch, Stewart, Kolasch & Birch, LLP

(57) ABSTRACT

The present invention is directed to compounds of formula I:

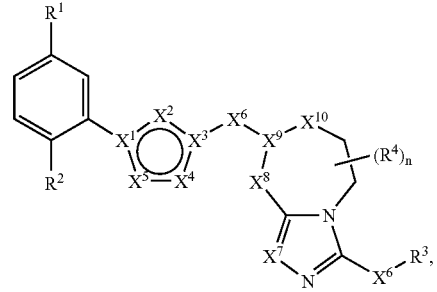

wherein $X^1$, $X^2$, $X^3$, $X^4$, $X^5$, $X^6$, $X^7$, $X^8$, $X^9$, $X^{10}$, $R^1$, $R^2$, $R^3$, $R^4$, and n are as defined for formula I in the description. The invention also relates to processes for the preparation of the compounds and to new intermediates employed in the preparation, pharmaceutical compositions containing the compounds, and to the use of the compounds in therapy.

16 Claims, No Drawings

OTHER PUBLICATIONS

Minakami et al., "Molecular Cloning and the Functional Expression of Two Isoforms of Human Metabotropic Glutamate Receptor Subtype 5", BBRC vol. 199, p. 1136- (1994).

Mittal et al., "Transient Lower Esophageal Sphincter Relaxation", Gastroenterology vol. 109, p. 601-610 (1995).

Nakanishi, "Metabotropic Glutamate Receptors: Synaptic Transmission, Modulation, and Plasticity", Neuron, vol. 13, p. 1031- (1994).

Neugerbauer, "Metabotropic glutamate receptors—important modulators of nociception and pain behavior", Pain, vol. 98, p. 1-8 (2002).

Pin et al., "Alternative splicing generates metabotropic glutamate receptors inducing different patterns of calcium release in *Xenopus* oocytes", PNAS vol. 89, p. 10331-10335 (1992).

Pin et al., "Review: Neurotransmitter receptors I, The metabotropic Glutamate Receptors: Structure and Functions", Neuropharmacology vol. 34, p. 1- (1995).

Schoepp et al., "Metabotropic glutamate receptors in brain function and pathology", Trends Pharmacol. Sci. vol. 14, p. 13-20 (1993).

Schoepp, "Novel Functions for Subtypes of Metabotropic Glutamate Receptors", Neurochem. Int. vol. 24 p. 439-449 (1994).

Spooren et al., "Novel allosteric antagonists shed light on mGlu5 receptors and CNS disorders", Trends Pharmacol. Sci. vol. 22, p. 331-337 (2001).

Van Herwaarden et al., "Diagnosis of reflux disease", Bailliere's Clin. Gastroenterol. vol. 14, p. 759-774 (2000).

Watkins et al., "Phenylglycine derivatives as antagonists of metabotropic glutamate receptors", Trends Pharmacol. Sci. vol. 15, p. 33-36 (1994).

FUSED HETEROCYCLIC COMPOUNDS AND THEIR USE AS METABOTROPIC GLUTAMATE RECEPTOR ANTAGONISTS

This application claims benefit under 35 U.S.C. 119(e) to provisional application 60/545,580, filed Feb. 19, 2004.

BACKGROUND OF THE INVENTION

The present invention relates to a new heterocyclic compounds, to pharmaceutical compositions containing the compounds and to the use of the compounds in therapies related to metabotropic glutamate receptor-mediated conditions. The present invention further relates to processes for the preparation of the compounds and to new intermediates used in the preparation thereof.

Glutamate is the major excitatory neurotransmitter in the mammalian central nervous system (CNS). Glutamate produces its effects on central neurons by binding to and thereby activating cell surface receptors. These receptors have been divided into two major classes, the ionotropic and metabotropic glutamate receptors, based on the structural features of the receptor proteins, the means by which the receptors transduce signals into the cell, and pharmacological profiles.

The metabotropic glutamate receptors (mGluRs) are G protein-coupled receptors that activate a variety of intracellular second messenger systems following the binding of glutamate. Activation of mGluRs in intact mammalian neurons elicits one or more of the following responses: activation of phospholipase C; increases in phosphoinositide (PI) hydrolysis; intracellular calcium release; activation of phospholipase D; activation or inhibition of adenyl cyclase; increases or decreases in the formation of cyclic adenosine monophosphate (cAMP); activation of guanylyl cyclase; increases in the formation of cyclic guanosine monophosphate (cGMP); activation of phospholipase $A_2$; increases in arachidonic acid release; and increases or decreases in the activity of voltage- and ligand-gated ion channels. Schoepp et al., *Trends Pharmacol. Sci.* 14:13 (1993), Schoepp, *Neurochem. Int.* 24:439 (1994), Pin et al., *Neuropharmacology* 34:1 (1995), Bordi and Ugolini, *Prog. Neurobiol.* 59:55 (1999). Eight distinct mGluR subtypes, termed mGluR1 through mGluR8, have been identified by molecular cloning. Nakanishi, *Neuron* 13:1031 (1994), Pin et al., *Neuropharmacology* 34:1 (1995), Knopfel et al., *J. Med. Chem.* 38:1417 (1995). Further receptor diversity occurs via expression of alternatively spliced forms of certain mGluR subtypes. Pin et al., *PNAS* 89:10331 (1992), Minakami et al., *BBRC* 199:1136 (1994), Joly et al., *J. Neurosci.* 15:3970 (1995). Metabotropic glutamate receptor subtypes may be subdivided into three groups, Group I, Group II, and Group III mGluRs, based on amino acid sequence homology, the second messenger systems utilized by the receptors, and by their pharmacological characteristics. Group I mGluR comprises mGluR1, mGluR5 and their alternatively spliced variants. The binding of agonists to these receptors results in the activation of phospholipase C and the subsequent mobilization of intracellular calcium.

Neurological, Psychiatric and Pain Disorders.

Attempts at elucidating the physiological roles of Group I mGluRs suggest that activation of these receptors elicits neuronal excitation. Various studies have demonstrated that Group I mGluRs agonists can produce postsynaptic excitation upon application to neurons in the hippocampus, cerebral cortex, cerebellum, and thalamus, as well as other CNS regions. Evidence indicates that this excitation is due to direct activation of postsynaptic mGluRs, but it also has been suggested that activation of presynaptic mGluRs occurs, resulting in increased neurotransmitter release. Baskys, *Trends Pharmacol. Sci.* 15:92 (1992), Schoepp, *Neurochem. Int.* 24:439 (1994), Pin et al., *Neuropharmacology* 34:1(1995), Watkins et al., *Trends Pharmacol. Sci.* 15:33 (1994).

Metabotropic glutamate receptors have been implicated in a number of normal processes in the mammalian CNS. Activation of mGluRs has been shown to be required for induction of hippocampal long-term potentiation and cerebellar long-term depression. Bashir et al., *Nature* 363:347 (1993), Bortolotto et al., *Nature* 368:740 (1994), Aiba et al., *Cell* 79:365 (1994), Aiba et al., *Cell* 79:377 (1994). A role for mGluR activation in nociception and analgesia also has been demonstrated. Meller et al., *Neuroreport* 4: 879 (1993), Bordi and Ugolini, *Brain Res.* 871:223 (1999). In addition, mGluR activation has been suggested to play a modulatory role in a variety of other normal processes including synaptic transmission, neuronal development, apoptotic neuronal death, synaptic plasticity, spatial learning, olfactory memory, central control of cardiac activity, waking, motor control and control of the vestibulo-ocular reflex. Nakanishi, *Neuron* 13:1031 (1994), Pin et al., *Neuropharmacology* 34:1, Knopfel et al., *J. Med. Chem.* 38:1417 (1995).

Further, Group I metabotropic glutamate receptors have been suggested to play roles in a variety of acute and chronic pathophysiological processes and disorders affecting the CNS. These include stroke, head trauma, anoxic and ischemic injuries, hypoglycemia, epilepsy, neurodegenerative disorders such as Alzheimer's disease, psychiatric disorders and pain. Schoepp et al., *Trends Pharmacol. Sci.* 14:13 (1993), Cunningham et al., *Life Sci.* 54:135 (1994), Hollman et al., *Ann. Rev. Neurosci.* 17:31 (1994), Pin et al., *Neuropharmacology* 34:1 (1995), Knopfel et al., *J. Med. Chem.* 38:1417 (1995), Spooren et al., *Trends Pharmacol. Sci.* 22:331 (2001), Gasparini et al. *Curr. Opin. Pharmacol.* 2:43 (2002), Neugebauer *Pain* 98:1 (2002). Much of the pathology in these conditions is thought to be due to excessive glutamate-induced excitation of CNS neurons. Because Group I mGluRs appear to increase glutamate-mediated neuronal excitation via postsynaptic mechanisms and enhanced presynaptic glutamate release, their activation probably contributes to the pathology. Accordingly, selective antagonists of Group I mGluR receptors could be therapeutically beneficial in all conditions underlain by excessive glutamate-induced excitation of CNS neurons, specifically as neuroprotective agents, analgesics or anticonvulsants. Recent advances in the elucidation of the neurophysiological roles of metabotropic glutamate receptors generally and Group I in particular, have established these receptors as promising drug targets in the therapy of acute and chronic neurological and psychiatric disorders and chronic and acute pain disorders.

Gastro Intestinal Disorders

The lower esophageal sphincter (LES) is prone to relaxing intermittently. As a consequence, fluid from the stomach can pass into the esophagus since the mechanical barrier is temporarily lost at such times, an event hereinafter referred to as "reflux".

Gastro-esophageal reflux disease (GERD) is the most prevalent upper gastrointestinal tract disease. Current pharmacotherapy aims at reducing gastric acid secretion, or at neutralizing acid in the esophagus. The major mechanism behind reflux has been considered to depend on a hypotonic lower esophageal sphincter. However, e.g. Holloway & Dent (1990) *Gastroenterol. Clin. N. Amer.* 19, pp. 517-535, has shown that most reflux episodes occur during transient lower esophageal sphincter relaxations (TLESRs), i.e. relaxations not triggered by swallows. It has also been shown that gastric acid secretion usually is normal in patients with GERD.

The novel compounds according to the present invention are useful for the inhibition of transient lower esophageal sphincter relaxations (TLESRs) and thus for treatment of gastro-esophageal reflux disorder (GERD).

The term "TLESR", transient lower esophageal sphincter relaxations, is herein defined in accordance with Mittal, R. K., Holloway, R. H., Penagini, R., Blackshaw, L. A., Dent, J., 1995; *Transient lower esophageal sphincter relaxation. Gastroenterology* 109, pp. 601-610.

The term "reflux" is herein defined as fluid from the stomach being able to pass into the esophagus, since the mechanical barrier is temporarily lost at such times. The term "GERD", gastro-esophageal reflux disease, is herein defined in accordance with van Heerwarden, M. A., Smout A. J. P. M, 2000; *Diagnosis of reflux disease. Baillière's Clin. Gastroenterol.* 14, pp. 759-774.

The physiological and pathophysiological significance of mGluR agonists and antagonists that display a high selectivity for mGluR subtypes, particularly the Group I receptor subtype, warrant a continued need for new agonists and antagonists.

SUMMARY OF THE INVENTION

The present invention relates to compounds of formula I:

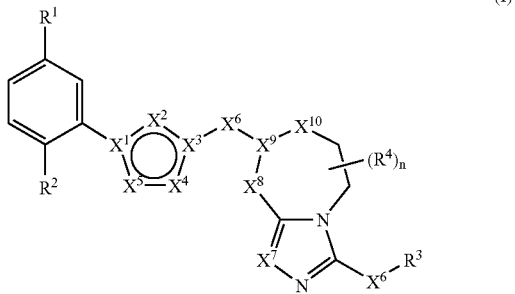

(I)

In Formula I, $X^1$, $X^2$, $X^3$, $X^4$, and $X^5$ are independently selected from the group consisting of C, $CR^5$, N, O, and S, wherein at least one of $X^1$, $X^2$, $X^3$, $X^4$, and $X^5$ is not N; $X^6$ is selected from the group consisting of a bond and $CR^5R^6$; $X^7$ is $CR^5$ or N; $X^8$ is selected from the group consisting of a bond, $CR^5R^6$, $NR^5$, O, S, SO, and $SO_2$; $X^9$ is $CR^5$ or N; and $X^{10}$ is selected from the group consisting of a bond, $CR^5R^6$, $(CR^5R^6)_2$, O, S, and $NR^5$.

$R^1$ is selected from the group consisting of hydroxy, halo, nitro, $C_{1-6}$alkylhalo, $OC_{1-6}$alkylhalo, $C_{1-6}$alkyl, $OC_{1-6}$alkyl, $C_{2-6}$alkenyl, $OC_{2-6}$alkenyl, $C_{2-6}$alkynyl, $OC_{2-6}$alkynyl, $C_{0-6}$alkyl$C_{3-6}$cycloalkyl, $OC_{0-6}$alkyl$C_{3-6}$cycloalkyl, $C_{0-6}$alkylaryl, $OC_{0-6}$alkylaryl, CHO, $(CO)R^5$, $O(CO)R^5$, $O(CO)OR^5$, $O(CN)OR^5$, $C_{1-6}$alkyl$OR^5$, $OC_{2-6}$alkyl$OR^5$, $C_{1-6}$alkyl$(CO)R^5$, $OC_{1-6}$alkyl$(CO)R^5$, $C_{0-6}$alkyl$CO_2R^5$, $OC_{1-6}$alkyl$CO_2R^5$, $C_{0-6}$alkylcyano, $OC_{2-6}$alkylcyano, $C_{0-6}$alkyl$NR^5R^6$, $OC_{2-6}$alkyl$NR^5R^6$, $C_{1-6}$alkyl$(CO)NR^5R^6$, $OC_{1-6}$alkyl$(CO)NR^5R^6$, $C_{0-6}$alkyl$NR^5(CO)R^6$, $OC_{2-6}$alkyl$NR^5(CO)R^6$, $C_{0-6}$alkyl$NR^5(CO)NR^5R^6$, $C_{0-6}$alkyl$SR^5$, $OC_{2-6}$alkyl$SR^5$, $C_{0-6}$alkyl$(SO)R^5$, $OC_{2-6}$alkyl$(SO)R^5$, $C_{0-6}$alkyl$SO_2R^5$, $OC_{2-6}$alkyl$SO_2R^5$, $C_{0-6}$alkyl$(SO_2)NR^5R^6$, $OC_{2-6}$alkyl$(SO_2)NR^5R^6$, $C_{0-6}$alkyl$NR^5(SO_2)R^6$, $OC_{2-6}$alkyl$NR^5(SO_2)R^6$, $C_{0-6}$alkyl$NR^5(SO_2)NR^5R^6$, $OC_{2-6}$alkyl$NR^5(SO_2)NR^5R^6$, $(CO)NR^5R^6$, $O(CO)NR^5R^6$, $NR^5OR^6$, $C_{0-6}$alkyl$NR^5(CO)OR^6$, $OC_{2-6}$alkyl$NR^5(CO)OR^6$, $SO_3R^5$ and a 5- or 6-membered ring containing atoms independently selected from the group consisting of C, N, O and S, wherein said ring may be substituted by one or more A, as defined below.

$R^2$ is selected from the group consisting of hydrogen, hydroxy, halo, nitro, $C_{1-6}$alkylhalo, $OC_{1-6}$alkylhalo, $C_{1-6}$alkyl, $OC_{1-6}$alkyl, $C_{2-6}$alkenyl, $OC_{2-6}$alkenyl, $C_{2-6}$alkynyl, $OC_{2-6}$alkynyl, $C_{0-6}$alkyl$C_{3-6}$cycloalkyl, $OC_{0-6}$alkyl$C_{3-6}$cycloalkyl, $C_{0-6}$alkylaryl, $OC_{0-6}$alkylaryl, CHO, $(CO)R^5$, $O(CO)R^5$, $O(CO)OR^5$, $O(CN)OR^5$, $C_{1-6}$alkyl$OR^5$, $OC_{2-6}$alkyl$OR^5$, $C_{1-6}$alkyl$(CO)R^5$, $OC_{1-6}$alkyl$(CO)R^5$, $C_{0-6}$alkyl$CO_2R^5$, $OC_{1-6}$alkyl$CO_2R^5$, $C_{0-6}$alkylcyano, $OC_{2-6}$alkylcyano, $C_{0-6}$alkyl$NR^5R^6$, $OC_{2-6}$alkyl$NR^5R^6$, $C_{1-6}$alkyl$(CO)NR^5R^6$, $OC_{1-6}$alkyl$(CO)NR^5R^6$, $C_{0-6}$alkyl$NR^5(CO)R^6$, $OC_{2-6}$alkyl$NR^5(CO)R^6$, $C_{0-6}$alkyl$NR^5(CO)NR^5R^6$, $C_{0-6}$alkyl$SR^5$, $OC_{2-6}$alkyl$SR^5$, $C_{0-6}$alkyl$(SO)R^5$, $OC_{2-6}$alkyl$(SO)R^5$, $C_{0-6}$alkyl$SO_2R^5$, $OC_{2-6}$alkyl$SO_2R^5$, $C_{0-6}$alkyl$(SO_2)NR^5R^6$, $OC_{2-6}$alkyl$(SO_2)NR^5R^6$, $C_{0-6}$alkyl$NR^5(SO_2)R^6$, $OC_{2-6}$alkyl$NR^5(SO_2)R^6$, $C_{0-6}$alkyl$NR^5(SO_2)NR^5R^6$, $OC_{2-6}$alkyl$NR^5(SO_2)NR^5R^6$, $(CO)NR^5R^6$, $O(CO)NR^5R^6$, $NR^5OR^6$, $C_{0-6}$alkyl$NR^5(CO)OR^6$, $OC_{2-6}$alkyl$NR^5(CO)OR^6$, $SO_3R^5$ and a 5- or 6-membered ring containing atoms independently selected from the group consisting of C, N, O and S, wherein said ring may be substituted by one or more A.

$R^3$ is a 5- or 6-membered ring containing atoms independently selected from the group consisting of C, N, O and S, wherein said ring may be substituted by one or more A.

$R^4$ is selected from the group consisting of hydroxy, halo, nitro, $C_{1-6}$alkylhalo, $OC_{1-6}$alkylhalo, $C_{1-6}$alkyl, $OC_{1-6}$alkyl, $C_{2-6}$alkenyl, $OC_{2-6}$alkenyl, $C_{2-6}$alkynyl, $OC_{2-6}$alkynyl, $C_{0-6}$alkyl$C_{3-6}$cycloalkyl, $OC_{0-6}$alkyl$C_{3-6}$cycloalkyl, $C_{0-6}$alkylaryl, $OC_{0-6}$alkylaryl, CHO, $(CO)R^5$, $O(CO)R^5$, $O(CO)OR^5$, $O(CN)OR^5$, $C_{1-6}$alkyl$OR^5$, $OC_{2-6}$alkyl$OR^5$, $C_{1-6}$alkyl$(CO)R^5$, $OC_{1-6}$alkyl$(CO)R^5$, $C_{0-6}$alkyl$CO_2R^5$, $OC_{1-6}$alkyl$CO_2R^5$, $C_{0-6}$alkylcyano, $OC_{2-6}$alkylcyano, $C_{0-6}$alkyl$NR^5R^6$, $OC_{2-6}$alkyl$NR^5R^6$, $C_{1-6}$alkyl$(CO)NR^5R^6$, $OC_{1-6}$alkyl$(CO)NR^5R^6$, $C_{0-6}$alkyl$NR^5(CO)R^6$, $OC_{2-6}$alkyl$NR^5(CO)R^6$, $C_{0-6}$alkyl$NR^5(CO)NR^5R^6$, $C_{0-6}$alkyl$SR^5$, $OC_{2-6}$alkyl$SR^5$, $C_{0-6}$alkyl$(SO)R^5$, $OC_{2-6}$alkyl$(SO)R^5$, $C_{0-6}$alkyl$SO_2R^5$, $OC_{2-6}$alkyl$SO_2R^5$, $C_{0-6}$alkyl$(SO_2)NR^5R^6$, $OC_{2-6}$alkyl$(SO_2)NR^5R^6$, $C_{0-6}$alkyl$NR^5(SO_2)R^6$, $OC_{2-6}$alkyl$NR^5(SO_2)R^6$, $C_{0-6}$alkyl$NR^5(SO_2)NR^5R^6$, $OC_{2-6}$alkyl$NR^5(SO_2)NR^5R^6$, $(CO)NR^5R^6$, $O(CO)NR^5R^6$, $NR^5OR^6$, $C_{0-6}$alkyl$NR^5(CO)OR^6$, $OC_{2-6}$alkyl$NR^5(CO)OR^6$, $SO_3R^5$ and a 5- or 6-membered ring containing atoms independently selected from the group consisting of C, N, O and S, wherein said ring may be substituted by one or more A.

$R^5$ and $R^6$ are independently selected from the group consisting of hydrogen, $C_{1-6}$alkyl, $C_{3-7}$cycloalkyl and aryl.

A is selected from the group consisting of hydrogen, hydroxy, halo, nitro, $C_{1-6}$alkylhalo, $OC_{1-6}$alkylhalo, $C_{1-6}$alkyl, $OC_{1-6}$alkyl, $C_{2-6}$alkenyl, $OC_{2-6}$alkenyl, $C_{2-6}$alkynyl, $OC_{2-6}$alkynyl, $C_{0-6}$alkyl$C_{3-6}$cycloalkyl, $OC_{0-6}$alkyl$C_{3-6}$cycloalkyl, $C_{0-6}$alkylaryl, $OC_{0-6}$alkylaryl, CHO, $(CO)R^5$, $O(CO)R^5$, $O(CO)OR^5$, $O(CN)OR^5$, $C_{1-6}$alkyl$OR^5$, $OC_{2-6}$alkyl$OR^5$, $C_{1-6}$alkyl$(CO)R^5$, $OC_{1-6}$alkyl$(CO)R^5$, $C_{0-6}$alkyl$CO_2R^5$, $OC_{1-6}$alkyl$CO_2R^5$, $C_{0-6}$alkylcyano, $OC_{2-6}$alkylcyano, $C_{0-6}$alkyl$NR^5R^5$, $OC_{2-6}$alkyl$NR^5R^8$, $C_{1-6}$alkyl$(CO)NR^5R^8$, $OC_{1-6}$alkyl$(CO)NR^5R^8$, $C_{0-6}$alkyl$NR^5(CO)R^8$, $OC_{2-6}$alkyl$NR^5(CO)R^8$, $C_{0-6}$alkyl$NR^5(CO)NR^5R^8$, $C_{0-6}$alkyl$SR^5$, $OC_{2-6}$alkyl$SR^5$, $C_{0-6}$alkyl$(SO)R^5$, $OC_{2-6}$alkyl$(SO)R^5$, $C_{0-6}$alkyl$SO_2R^5$, $OC_{2-6}$alkyl$SO_2R^5$, $C_{0-6}$alkyl$(SO_2)NR^5R^8$, $OC_{2-6}$alkyl$(SO_2)NR^5R^8$, $C_{0-6}$alkyl$NR^5(SO_2)R^8$, $OC_{2-6}$alkyl$NR^5(SO_2)R^8$, $C_{0-6}$alkyl$NR^5(SO_2)NR^5R^8$, $OC_{2-6}$alkyl$NR^5(SO_2)NR^5R^8$, $(CO)NR^5R^8$, $O(CO)NR^5R^8$, $NR^5OR^8$, $C^{0-6}$alkyl$NR^5(CO)OR^8$, $OC_{2-6}$alkyl$NR^5(CO)OR^8$, $SO_3R^5$ and a 5- or 6-membered ring containing atoms independently selected from the group consisting of C, N, O and S.

Variable n is 0, 1, 2, 3, or 4.

In a further aspect of the invention there is provided pharmaceutical compositions comprising a therapeutically effective amount of a compound of formula I and a pharmaceutically acceptable diluent, excipient and/or inert carrier.

In yet a further aspect of the invention there is provided a pharmaceutical composition comprising a compound of formula I for use in the treatment of mGluR5 receptor mediated disorders, and for use in the treatment of neurological disorders, psychiatric disorders, gastrointestinal disorders and pain disorders.

In still a further aspect of the invention there is provided the compound of formula I for use in therapy, especially for the treatment of mGluR5 receptor mediated disorders, and for the treatment of neurological disorders, psychiatric disorders, gastrointestinal disorders and pain disorders.

A further aspect of the invention is the use of a compound according to formula I for the manufacture of a medicament for the treatment or prevention of obesity and obesity related conditions, as well as treating eating disorders by inhibition of excessive food intake and the resulting obesity and complications associated therewith.

In another aspect of the invention there is provided processes for the preparation of compounds of formula I and the intermediates used in the preparation thereof.

These and other aspects of the present invention are described in greater detail herein below.

DETAILED DESCRIPTION OF THE PREFERRED EMBODIMENTS

The object of the present invention is to provide compounds exhibiting an activity at metabotropic glutamate receptors (mGluRs), especially at the mGluR5 receptors. Listed below are definitions of various terms used in the specification and claims to describe the present invention.

For the avoidance of doubt it is to be understood that where in this specification a group is qualified by 'hereinbefore defined', 'defined hereinbefore' or 'defined above' said group encompasses the first occurring and broadest definition as well as each and all of the other definitions for that group.

For the avoidance of doubt it is to be understood that in this specification '$C_{1-6}$' means a carbon group having 1, 2, 3, 4, 5 or 6 carbon atoms. Similarly '$C_{1-3}$' means a carbon group having 1, 2, or 3 carbon atoms In the case where a subscript is the integer 0 (zero) the group to which the subscript refers indicates that the group is absent.

In this specification, unless stated otherwise, the term "alkyl" includes both straight and branched chain alkyl groups and may be, but are not limited to methyl, ethyl, n-propyl, i-propyl, n-butyl, i-butyl, s-butyl, t-butyl, n-pentyl, i-pentyl, t-pentyl, neo-pentyl, n-hexyl or i-hexyl, t-hexyl. The term $C_{1-3}$alkyl has 1 to 3 carbon atoms and may be methyl, ethyl, n-propyl or i-propyl.

In this specification, unless stated otherwise, the term "cycloalkyl" refers to an optionally substituted, saturated cyclic hydrocarbon ring system. The term "$C_{3-7}$cycloalkyl" may be cyclopropyl, cyclobutyl, cyclopentyl, cyclohexyl or cycloheptyl.

In this specification, unless stated otherwise, the term "alkoxy" includes both straight or branched alkoxy groups. $C_{1-3}$alkoxy may be, but is not limited to methoxy, ethoxy, n-propoxy or i-propoxy.

In this specification, unless stated otherwise, the term "bond" may be a saturated or unsaturated bond.

In this specification, unless stated otherwise, the term "halo" and "halogen" may be fluoro, chloro, bromo or iodo.

In this specification, unless stated otherwise, the term "alkylhalo" means an alkyl group as defined above, which is substituted with halo as described above. The term "$C_{1-6}$alkylhalo" may include, but is not limited to fluoromethyl, difluoromethyl, trifluoromethyl, fluoroethyl, difluoroethyl or bromopropyl. The term "$OC_{1-6}$alkylhalo" may include, but is not limited to fluoromethoxy, difluoromethoxy, trifluoromethoxy, fluoroethoxy or difluoroethoxy.

In this specification, unless stated otherwise, the term "alkenyl" includes both straight and branched chain alkenyl groups. The term "$C_{2-6}$alkenyl" refers to an alkenyl group having 2 to 6 carbon atoms and one or two double bonds, and may be, but is not limited to vinyl, allyl, propenyl, i-propenyl, butenyl, i-butenyl, crotyl, pentenyl, i-pentenyl and hexenyl.

In this specification, unless stated otherwise, the term "alkynyl" includes both straight and branched chain alkynyl groups. The term $C_{2-6}$alkynyl having 2 to 6 carbon atoms and one or two triple bonds, and may be, but is not limited to ethynyl, propargyl, butynyl, i-butynyl, pentynyl, i-pentynyl and hexynyl.

In this specification unless otherwise stated the term "aryl" refers to an optionally substituted monocyclic or bicyclic hydrocarbon ring system containing at least one unsaturated aromatic ring. Examples and suitable values of the term "aryl" are phenyl, naphthyl, 1,2,3,4-tetrahydronaphthyl, indyl and indenyl.

In this specification, unless stated otherwise, the term "heteroaryl" refers to an optionally substituted monocyclic or bicyclic unsaturated, ring system containing at least one heteroatom selected independently from N, O or S. Examples of "heteroaryl" may be, but are not limited to thiophene, thienyl, pyridyl, thiazolyl, furyl, pyrrolyl, triazolyl, imidazolyl, oxadiazolyl, oxazolyl, isoxazolyl, pyrazolyl, imidazolonyl, oxazolonyl, thiazolonyl, tetrazolyl and thiadiazolyl, benzoimidazolyl, benzooxazolyl, tetrahydrotriazolopyridyl, tetrahydrotriazolopyrimidinyl, benzofuryl, indolyl, isoindolyl, pyridonyl, pyridazinyl, pyrimidinyl, imidazopyridyl, oxazolopyridyl, thiazolopyridyl, pyridyl, imidazopyridazinyl, oxazolopyridazinyl, thiazolopyridazinyl and purinyl.

In this specification, unless stated otherwise, the term "alkylaryl", "alkylheteroaryl" and "alkylcycloalkyl" refer to a substituent that is attached via the alkyl group to an aryl, heteroaryl and cycloalkyl group. In this specification, unless stated otherwise, the term "heterocycloalkyl" refers to an optionally substituted, saturated cyclic hydrocarbon ring system wherein one or more of the carbon atoms are replaced with heteroatom. The term "heterocycloalkyl" includes but is not limited to pyrrolidine, tetrahydrofuran, tetrahydrothiophene, piperidine, piperazine, morpholine, thiomorpholine, tetrahydropyran, tetrahydrothiopyran.

In this specification, unless stated otherwise the term "5- or 6-membered ring containing atoms independently selected from C, N, O or S", includes aromatic and heteroaromatic rings as well as carbocyclic and heterocyclic rings, which may be saturated, partially saturated or unsaturated. Examples of such rings may be, but are not limited to furyl, isoxazolyl, isothiazolyl, oxazolyl, pyrazinyl, pyrazolyl, pyridazinyl, pyridyl, pyrimidyl, pyrrolyl, thiazolyl, thienyl, imidazolyl, imidazolidinyl, imidazolinyl, triazolyl, morpholinyl, piperazinyl, piperidyl, piperidonyl, pyrazolidinyl, pyrazolinyl, pyrrolidinyl, pyrrolinyl, tetrahydropyranyl, thiomorpholinyl, phenyl, cyclohexyl, cyclopentyl and cyclohexenyl.

In this specification, unless stated otherwise, the term "=NR$^5$" and "=NOR$^5$" include imino- and oximo-groups carrying an R$^5$ substituent and may be, or be part of, groups including, but not limited to iminoalkyl, iminohydroxy, iminoalkoxy, amidine, hydroxyamidine and alkoxyamidine.

In the case where a subscript is the integer 0 (zero) the group to which the subscript refers, indicates that the group is absent, i.e. there is a direct bond between the groups. In this specification unless stated otherwise the term "fused rings" refers to two rings which share 2 common atoms.

In this specification, unless stated otherwise, the term "bridge" means a molecular fragment, containing one or more atoms, or a bond, which connects two remote atoms in a ring, thus forming either bi- or tricyclic systems.

One embodiment of the invention relates to compounds of Formula I and their pharmaceutically acceptable salts and hydrates:

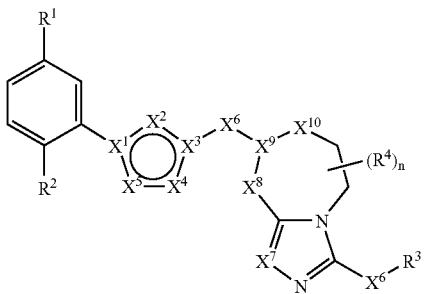

(I)

In Formula I, X$^1$, X$^2$, X$^3$, X$^4$, and X$^5$ are independently selected from the group consisting of C, CR$^5$, N, O, and S, wherein at least one of X$^1$, X$^2$, X$^3$, X$^4$, and X$^5$ is not N; X$^6$ is selected from the group consisting of a bond and CR$^5$R$^6$; X$^7$ is CR$^5$ or N, preferably N; X$^8$ is selected from the group consisting of a bond, CR$^5$R$^6$, NR$^5$, O, S, SO, and SO$_2$. Preferably, X$^8$ is a bond, CR$^5$R$^6$, NR$^5$, O, or S. X$^9$ is CR$^5$ or N and X$^{10}$ is selected from the group consisting of a bond, CR$^5$R$^6$, (CR$^5$R$^6$)$_2$, O, S, and NR$^5$, preferably a bond, CR$^5$R$^6$, (CR$^5$R$^6$)$_2$, O, or S.

R$^1$ is selected from the group consisting of hydroxy, halo, nitro, C$_{1-6}$alkylhalo, OC$_{1-6}$alkylhalo, C$_{1-6}$alkyl, OC$_{1-6}$alkyl, C$_{2-6}$alkenyl, OC$_{2-6}$alkenyl, C$_{2-6}$alkynyl, OC$_{2-6}$alkynyl, C$_{0-6}$alkylC$_{3-6}$cycloalkyl, OC$_{0-6}$alkylC$_{3-6}$cycloalkyl, C$_{0-6}$alkylaryl, OC$_{0-6}$alkylaryl, CHO, (CO)R$^5$, O(CO)R$^5$, O(CO)OR$^5$, O(CN)OR$^5$, C$_{1-6}$alkylOR$^5$, OC$_{2-6}$alkylOR$^5$, C$_{1-6}$alkyl(CO)R$^5$, OC$_{1-6}$alkyl(CO)R$^5$, C$_{0-6}$alkylCO$_2$R$^5$, OC$_{1-6}$alkylCO$_2$R$^5$, C$_{0-6}$alkylcyano, OC$_{2-6}$alkylcyano, C$_{0-6}$alkylNR$^5$R$^6$, OC$_{2-6}$alkylNR$^5$R$^6$, C$_{1-6}$alkyl(CO)NR$^5$R$^6$, OC$_{1-6}$alkyl(CO)NR$^5$R$^6$, C$_{0-6}$alkylNR$^5$(CO)R$^6$, OC$_{2-6}$alkylNR$^5$(CO)R$^6$, C$_{0-6}$alkylNR$^5$(CO)NR$^5$R$^6$, C$_{0-6}$alkylSR$^5$, OC$_{2-6}$alkylSR$^5$, C$_{0-6}$alkyl(SO)R$^5$, OC$_{2-6}$alkyl(SO)R$^5$, C$_{0-6}$alkylSO$_2$R$^5$, OC$_{2-6}$alkylSO$_2$R$^5$, C$_{0-6}$alkyl(SO$_2$)NR$^5$R$^6$, OC$_{2-6}$alkyl(SO$_2$)NR$^5$R$^6$, C$_{0-6}$alkylNR$^5$(SO$_2$)R$^6$, OC$_{2-6}$alkylNR$^5$(SO$_2$)R$^6$, C$_{0-6}$alkylNR$^5$(SO$_2$)NR$^5$R$^6$, OC$_{2-6}$alkylNR$^5$(SO$_2$)NR$^5$R$^6$, (CO)NR$^5$R$^6$, O(CO)NR$^5$R$^6$, NR$^5$OR$^6$, C$_{0-6}$alkylNR$^5$(CO)OR$^6$, OC$_{2-6}$alkylNR$^5$(CO)OR$^6$, SO$_3$R$^5$ and a 5- or 6-membered ring containing atoms independently selected from the group consisting of C, N, O and S, wherein said ring may be substituted by one or more A, as defined below. Preferably, R$^1$ is halo, C$_{1-6}$alkylhalo, C$_{1-6}$alkyl, OC$_{1-6}$alkyl, or C$_{0-6}$alkylcyano.

R$^2$ is selected from the group consisting of hydrogen, hydroxy, halo, nitro, C$_{1-6}$alkylhalo, OC$_{1-6}$alkylhalo, C$_{1-6}$alkyl, OC$_{1-6}$alkyl, C$_{2-6}$alkenyl, OC$_{2-6}$alkenyl, C$_{2-6}$alkynyl, OC$_{2-6}$alkynyl, C$_{0-6}$alkylC$_{3-6}$cycloalkyl, OC$_{0-6}$alkylC$_{3-6}$cycloalkyl, C$_{0-6}$alkylaryl, OC$_{0-6}$alkylaryl, CHO, (CO)R$^5$, O(CO)R$^5$, O(CO)OR$^5$, O(CN)OR$^5$, C$_{1-6}$alkylOR$^5$, OC$_{2-6}$alkylOR$^5$, C$_{1-6}$alkyl(CO)R$^5$, OC$_{1-6}$alkyl(CO)R$^5$, C$_{0-6}$alkylCO$_2$R$^5$, OC$_{1-6}$alkylCO$_2$R$^5$, C$_{0-6}$alkylcyano, OC$_{2-6}$alkylcyano, C$_{0-6}$alkylNR$^5$R$^6$, OC$_{2-6}$alkylNR$^5$R$^6$, C$_{1-6}$alkyl(CO)NR$^5$R$^6$, OC$_{1-6}$alkyl(CO)NR$^5$R$^6$, C$_{0-6}$alkylNR$^5$(CO)R$^6$, OC$_{2-6}$alkylNR$^5$(CO)R$^6$, C$_{0-6}$alkylNR$^5$(CO)NR$^5$R$^6$, C$_{0-6}$alkylSR$^5$, OC$_{2-6}$alkylSR$^5$, C$_{0-6}$alkyl(SO)R$^5$, OC$_{2-6}$alkyl(SO)R$^5$, C$_{0-6}$alkylSO$_2$R$^5$, OC$_{2-6}$alkylSO$_2$R$^5$, C$_{0-6}$alkyl(SO$_2$)NR$^5$R$^6$, OC$_{2-6}$alkyl(SO$_2$)NR$^5$R$^6$, C$_{0-6}$alkylNR$^5$(SO$_2$)R$^6$, OC$_{2-6}$alkylNR$^5$(SO$_2$)R$^6$, C$_{0-6}$alkylNR$^5$(SO$_2$)NR$^5$R$^6$, OC$_{2-6}$alkylNR$^5$(SO$_2$)NR$^5$R$^6$, (CO)NR$^5$R$^6$, O(CO)NR$^5$R$^6$, NR$^5$OR$^6$, C$_{0-6}$alkylNR$^5$(CO)OR$^6$, OC$_{2-6}$alkylNR$^5$(CO)OR$^6$, SO$_3$R$^5$ and a 5- or 6-membered ring containing atoms independently selected from the group consisting of C, N, O and S, wherein said ring may be substituted by one or more A. Preferably, R$^2$ is hydrogen or halo.

R$^3$ is a 5- or 6-membered ring containing atoms independently selected from the group consisting of C, N, O and S, wherein said ring may be substituted by one or more A. Preferably, R$^3$ is a 6-membered ring.

R$^4$ is selected from the group consisting of hydroxy, halo, nitro, C$_{1-6}$alkylhalo, OC$_{1-6}$alkylhalo, C$_{1-6}$alkyl, OC$_{1-6}$alkyl, C$_{2-6}$alkenyl, OC$_{2-6}$alkenyl, C$_{2-6}$alkynyl, OC$_{2-6}$alkynyl, C$_{0-6}$alkylC$_{3-6}$cycloalkyl, OC$_{0-6}$alkylC$_{3-6}$cycloalkyl, C$_{0-6}$alkylaryl, OC$_{0-6}$alkylaryl, CHO, (CO)R$^5$, O(CO)R$^5$, O(CO)OR$^5$, O(CN)OR$^5$, C$_{1-6}$alkylOR$^5$, OC$_{2-6}$alkylOR$^5$, C$_{1-6}$alkyl(CO)R$^5$, OC$_{1-6}$alkyl(CO)R$^5$, C$_{0-6}$alkylCO$_2$R$^5$, OC$_{1-6}$alkylCO$_2$R$^5$, C$_{0-6}$alkylcyano, OC$_{2-6}$alkylcyano, C$_{0-6}$alkylNR$^5$R$^6$, OC$_{2-6}$alkylNR$^5$R$^6$, C$_{1-6}$alkyl(CO)NR$^5$R$^6$, OC$_{1-6}$alkyl(CO)NR$^5$R$^6$, C$_{0-6}$alkylNR$^5$(CO)R$^6$, OC$_{2-6}$alkylNR$^5$(CO)R$^6$, C$_{0-6}$alkylNR$^5$(CO)NR$^5$R$^6$, C$_{0-6}$alkylSR$^5$, OC$_{2-6}$alkylSR$^5$, C$_{0-6}$alkyl(SO)R$^5$, OC$_{2-6}$alkyl(SO)R$^5$, C$_{0-6}$alkylSO$_2$R$^5$, OC$_{2-6}$alkylSO$_2$R$^5$, C$_{0-6}$alkyl(SO$_2$)NR$^5$R$^6$, OC$_{2-6}$alkyl(SO$_2$)NR$^5$R$^6$, C$_{0-6}$alkylNR$^5$(SO$_2$)R$^6$, OC$_{2-6}$alkylNR$^5$(SO$_2$)R$^6$, C$_{0-6}$alkylNR$^5$(SO$_2$)NR$^5$R$^6$, OC$_{2-6}$alkylNR$^5$(SO$_2$)NR$^5$R$^6$, (CO)NR$^5$R$^6$, O(CO)NR$^5$R$^6$, NR$^5$OR$^6$, C$_{0-6}$alkylNR$^5$(CO)OR$^6$, OC$_{2-6}$alkylNR$^5$(CO)OR$^6$, SO$_3$R$^5$ and a 5- or 6-membered ring containing atoms independently selected from the group consisting of C, N, O and S, wherein said ring may be substituted by one or more A. R$^4$, when not hydrogen, preferably is C$_{1-6}$alkylhalo or C$_{1-6}$alkyl.

R$^5$ and R$^6$ are independently selected from the group consisting of hydrogen, C$_{1-6}$alkyl, C$_{3-7}$cycloalkyl and aryl. Preferably, R$^5$ and R$^6$ are selected from hydrogen and C$_{1-6}$alkyl.

A is selected from the group consisting of hydrogen, hydroxy, halo, nitro, C$_{1-6}$alkylhalo, OC$_{1-6}$alkylhalo, C$_{1-6}$alkyl, OC$_{1-6}$alkyl, C$_{2-6}$alkenyl, OC$_{2-6}$alkenyl, C$_{2-6}$alkynyl, OC$_{2-6}$alkynyl, C$_{0-6}$alkylC$_{3-6}$cycloalkyl, OC$_{0-6}$alkylC$_{3-6}$cycloalkyl, C$_{0-6}$alkylaryl, OC$_{0-6}$alkylaryl, CHO, (CO)R$^5$, O(CO)R$^5$, O(CO)OR$^5$, O(CN)OR$^5$, C$_{1-6}$alkylOR$^5$, OC$_{2-6}$alkylOR$^5$, C$_{1-6}$alkyl(CO)R$^5$, OC$_{1-6}$alkyl(CO)R$^5$, C$_{0-6}$alkylCO$_2$R$^5$, OC$_{1-6}$alkylCO$_2$R$^5$, C$_{0-6}$alkylcyano, OC$_{2-6}$alkylcyano, C$_{0-6}$alkylNR$^5$R$^5$, OC$_{2-6}$alkylNR$^5$R$^8$, C$_{1-6}$alkyl(CO)NR$^5$R$^8$, OC$_{1-6}$alkyl(CO)NR$^5$R$^8$, C$_{0-6}$alkylNR$^5$(CO)R$^8$, OC$_{2-6}$alkylNR$^5$(CO)R$^8$, C$_{0-6}$alkylNR$^5$(CO)NR$^5$R$^8$, C$_{0-6}$alkylSR$^5$, OC$_{2-6}$alkylSR$^5$, C$_{0-6}$alkyl(SO)R$^5$, OC$_{2-6}$alkyl(SO)R$^5$, C$_{0-6}$alkylSO$_2$R$^5$, OC$_{2-6}$alkylSO$_2$R$^5$, C$_{0-6}$alkyl(SO$_2$)NR$^5$R$^8$, OC$_{2-6}$alkyl(SO$_2$)NR$^5$R$^8$, C$_{0-6}$alkylNR$^5$(SO$_2$)R$^8$, OC$_{2-6}$alkylNR$^5$(SO$_2$)R$^8$, C$_{0-6}$alkylNR$^5$(SO$_2$)NR$^5$R$^8$, OC$_{2-6}$alkylNR$^5$(SO$_2$)NR$^5$R$^8$, (CO)NR$^5$R$^8$, O(CO)NR$^5$R$^8$, NR$^5$OR$^8$, C$_{0-6}$alkylNR$^5$(CO)OR$^8$, OC$_{2-6}$alkylNR$^5$(CO)OR$^8$, SO$_3$R$^5$ and a 5- or 6-membered ring containing atoms independently selected from the group consisting of C, N, O and S. Preferred values for A are hydrogen and halo.

Variable n is 0, 1, 2, 3, or 4. Preferably, n is 0, 1, or 2.

It is understood that a) when X2=X4=X5=N, and either of X8 or X10 is a bond, then X9 is not N, b) when $X^7$ is N at least two of $X^1, X^2, X^3, X^4$, and $X^5$ are not N, and c) $X^1$ and $X^3$ are not O.

It is also understood that the invention does not encompass the following compounds:

- 8-[5-(3-Chloro-phenyl)-[1,2,4]oxadiazol-3-ylmethyl]-3-pyridine-4-yl-5,6,7,8-tetrahydro-[1,2,4]triazolo[4,3-a]pyridine,
- 8-[5-(3-Chloro-phenyl)-[1,2,4]oxadiazol-3-ylmethyl]-3-thiophen-2-yl-5,6,7,8-tetrahydro-[1,2,4]triazolo[4,3-a]pyridine,
- 8-[5-(5-Chloro-2-fluoro-phenyl)-[1,2,4]oxadiazol-3-ylmethyl]-3-pyridine-4-yl-5,6,7,8-tetrahydro[1,2,4]triazolo[4,3-a]pyridine,
- 8-[5-(3-Chloro-phenyl)-[1,2,4]oxadiazol-3-ylmethyl]-3-pyridine-4-yl-5,6,7,8-tetrahydro-[1,2,4]triazolo[4,3-a]pyrimidine,
- 8-[5-(5-Chloro-2-fluoro-phenyl)-[1,2,4]oxadiazol-3ylmethyl]-3-pyridine-4-yl-5,6,7,8-tetrahydro-[1,2,4]triazolo[4,3-a]pyrimidine,
- 8-[5-(3-Chloro-phenyl)-[1,3,4]oxadiazol-2-ylmethyl]-3-pyridine-4-yl-5,6,7,8-tetrahydro-[1,2,4]triazolo[4,3-a]pyrimidine,
- 8-{1-[5-(3-Chloro-phenyl)-[1,3,4]oxadiazol-2-yl]-ethyl}-3-pyridin-4-yl-5,6,7,8-tetrahydro-[1,2,4]triazolo[4,3-a]pyrimidine,
- 8-[5-(5-Chloro-phenyl)-[1,2,4]oxadiazol-3-ylmethyl]-3-furan-2-yl-5,6,7,8-tetrahydro-[1,2,4]triazolo[4,3-a]pyrimidine,
- 8-{1-[5-(3-Chloro-phenyl)-[1,2,4]oxadiazol-3-yl]-ethyl}-3-pyridin-4-yl-5,6,7,8-tetrahydro-[1,2,4]triazolo[4,3-a]pyrimidine,
- 3-Pyridin-4-yl-8-[1-(5-m-tolyl-[1,2,4]oxadiazol-3-yl)-ethyl]-5,6,7,8-tetrahydro -[1,2,4]triazolo[4,3-a]pyrimidine,
- (+)-8-{(1S)-1-[5-(3-chlorophenyl)-1,2,4-oxadiazol-3-yl]ethyl}-3-pyridin-4-yl-5,6,7,8-tetrahydro[1,2,4]triazolo[4,3-a]pyrimidine,
- (−)-8-{(1R)-1-[5-(3-chlorophenyl)-1,2,4-oxadiazol-3-yl]ethyl}-3-pyridin-4-yl-5,6,7,8-tetrahydro[1,2,4]triazolo[4,3-a]pyrimidine,
- 3-[5-(3-Pyridin-4-yl-6,7-dihydro-5H-[1,2,4]triazolo[4,3-α]pyrimidin-8-ylmethyl)[1,3,4]oxadiazol-2-yl]benzonitrile,
- 3-{5-[3-(2-Methoxypyridin-4-yl)-6,7-dihydro-5H-[1,2,4]triazolo[4,3-α]pyrimidin-8-ylmethyl][1,3,4]oxadiazol-2-yl}benzonitrile,
- 3-{5-[3-(2-Methoxy-pyridin-4-yl)-6,7-dihydro-5H-[1,2,4]triazolo[4,3-a]pyrimidin-8-ylmethyl]-[1,2,4]oxadiazol-3-yl}-benzonitrile,
- 3-{3-[(3-pyridin-4-yl-6,7-dihydro[1,2,4]triazolo[4,3-α]pyrimidin-8(5H)-yl)methyl]-1,2,4-oxadiazol-5-yl}benzonitrile,
- 3-(3-{[3-(2-methoxypyridin-4-yl)-6,7-dihydro[1,2,4]triazolo[4,3-α]pyrimidin-8(5H)-yl]methyl}-1,2,4-oxadiazol-5-yl)benzonitrile,
- 3-{5-[(3-pyridin-4-yl-6,7-dihydro[1,2,4]triazolo[4,3-a]pyrimidin-8(5H) -yl)methyl]-1,2,4-oxadiazol-3yl}benzonitrile, and
- 3-{5-[3-(2-Hydroxy-pyridin-4-yl)-6,7-dihydro-5H-[1,2,4]triazolo[4,3-a]pyrimidin-8-ylmethyl]-[1,2,4]oxadiazol-3-yl}-benzonitrile.

A subset of preferred compounds correspond to formula II:

(II)

In formula II, the structural variables are as defined in formula I. In this context, $X^7$ preferably is N.

Another subset of preferred compounds correspond to formula III:

(III)

In formula III, the structural variables are as defined in formula I. Preferably, $X^3$ is C or N.

In other embodiments of the invention, the ring containing $X^1, X^2, X^3, X^4$, and $X^5$ is selected from the group consisting of:

Preferably, the ring is either:

In these embodiments, $X^7$ preferably is N, while $X^8$ is preferably a bond. In one subset of compounds, $X^9$ is $CR^5$, and $X^{10}$ is $NR^5$, O, $CR^5R^6$, or $(CR^5R^6)_2$.

In another subset of compounds, $X^8$ is preferably S. In this scenario, $X^9$ preferably is $CR^5$, while $X^{10}$ is a bond. In other embodiments, $X^9$ is N.

In yet other embodiments of the invention, the fused ring containing $X^7$, $X^8$, $X^9$, and $X^{10}$ is selected from the group consisting of:

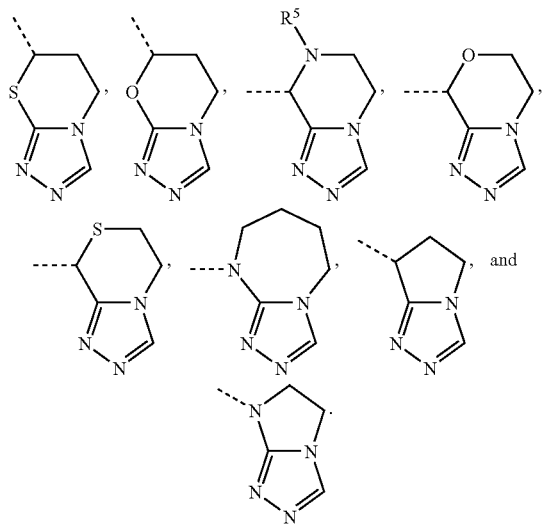

Certain other embodiments of the invention are represented by the following exemplary compounds:

- 7-[5-(5-Chloro-2-fluorophenyl)-1,2,4-oxadiazol-3-yl]-3-(2-thienyl)-6,7-dihydro-5H-[1,2,4]triazolo[3,4-b][1,3]thiazine,
- 9-{[5-(3-chlorophenyl)-1,2,4-oxadiazol-3-yl]methyl}-3-pyridin-4-yl-6,7,8,9-tetrahydro-5H-[1,2,4]triazolo[4,3-a][1,3]diazepine,
- 9-{1-[5-(3-chlorophenyl)-1,2,4-oxadiazol-3-yl]ethyl}-3-pyridin-4-yl-6,7,8,9-tetrahydro-5H-[1,2,4]triazolo[4,3-a][1,3]diazepine,
- 7-{[5-(3-chlorophenyl)-1,2,4-oxadiazol-3-yl]methyl}-3-pyridin-4-yl-6,7-dihydro-5H-pyrrolo[2,1-c][1,2,4]triazole,
- 9-{[5-(3-chlorophenyl)-1,2,4-oxadiazol-3-yl]methyl}-3-(trifluoromethyl)-6,7,8,9-tetrahydro-5H-[1,2,4]triazolo[4,3-a][1,3]diazepine,
- 8-[3-(3-Chloro-phenyl)-[1,2,4]oxadiazol-5-yl]-3-(4-methoxy-phenyl)-5,6,7,8-tetrahydro-[1,2,4]triazolo[4,3-a]pyrazine,
- 8-[3-(3-Chloro-phenyl)-[1,2,4]oxadiazol-5-yl]-3-(4-methoxy-phenyl)-7-methyl-5,6,7,8-tetrahydro-[1,2,4]triazolo[4,3-a]pyrazine,
- 9-{[5-(3-chlorophenyl)isoxazol-3-yl]methyl}-3-(3,5-difluorophenyl)-6,7,8,9-tetrahydro-5H-[1,2,4]triazolo[4,3-a][1,3]diazepine,
- 9-{[5-(3-chlorophenyl)isoxazol-3-yl]methyl}-3-(4-methoxyphenyl)-6,7,8,9-tetrahydro-5H-[1,2,4]triazolo[4,3-a][1,3]diazepine,
- 9-{[5-(3-chlorophenyl)isoxazol-3-yl]methyl}-3-pyridin-4-yl-6,7,8,9-tetrahydro-5H-[1,2,4]triazolo[4,3-a][1,3]diazepine,
- 9-{[5-(5-chloro-2-fluorophenyl)-1,2,4-oxadiazol-3-yl]methyl}-3-pyridin-4-yl-6,7,8,9-tetrahydro-5H-[1,2,4]triazolo[4,3-a][1,3]diazepine,
- 9-{[5-(3-chlorophenyl)-1,2,4-oxadiazol-3-yl]methyl}-3-(3,5-difluorophenyl)-6,7,8,9-tetrahydro-5H-[1,2,4]triazolo[4,3-a][1,3]diazepine, and
- 9-{[5-(3-chlorophenyl)-1,2,4-oxadiazol-3-yl]methyl}-3-(4-methoxyphenyl)-6,7,8,9-tetrahydro-5H-[1,2,4]triazolo[4,3-a][1,3]diazepine and pharmaceutically acceptable salts thereof.

Embodiments of the invention include salt forms of the compounds of Formula I. Salts for use in pharmaceutical compositions will be pharmaceutically acceptable salts, but other salts may be useful in the production of the compounds of Formula I. A suitable pharmaceutically acceptable salt of the compounds of the invention is, for example, an acid-addition salt, for example an inorganic or organic acid. In addition, a suitable pharmaceutically acceptable salt of the compounds of the invention is an alkali metal salt, an alkaline earth metal salt or a salt with an organic base. Other pharmaceutically acceptable salts and methods of preparing these salts may be found in, for example, Remington's Pharmaceutical Sciences (18$^{th}$ Edition, Mack Publishing Co.) 1990.

Some compounds of formula I may have chiral centres and/or geometric isomeric centres (E- and Z-isomers), and it is to be understood that the invention encompasses all such optical, diastereoisomeric and geometric isomers.

The invention also relates to any and all tautomeric forms of the compounds of Formula I.

The invention further relates to hydrate and solvate forms of the compounds of Formula I.

Pharmaceutical Composition

According to one aspect of the present invention there is provided a pharmaceutical composition comprising as active ingredient a therapeutically effective amount of the compound of Formula I, or salts, solvates or solvated salts thereof, in association with one or more pharmaceutically acceptable diluent, excipients and/or inert carrier. The composition may be in a form suitable for oral administration, for example as a tablet, pill, syrup, powder, granule or capsule, for parenteral injection (including intravenous, subcutaneous, intramuscular, intravascular or infusion) as a sterile solution, suspension or emulsion, for topical administration e.g. as an ointment, patch or cream or for rectal administration e.g. as a suppository.

In general the above compositions may be prepared in a conventional manner using one or more conventional excipients, pharmaceutical acceptable diluents and/or inert carriers.

Suitable daily doses of the compounds of formula I in the treatment of a mammal, including man are approximately 0.01 to 250 mg/kg bodyweight at peroral administration and about 0.001 to 250 mg/kg bodyweight at parenteral administration. The typical daily dose of the active ingredients varies within a wide range and will depend on various factors such as the relevant indication, severity of the illness being treated, the route of administration, the age, weight and sex of the patient and the particular compound being used, and may be determined by a physician.

Medical Use

It has been found that the compounds according to the present invention, exhibit a high degree of potency and selectivity for individual metabotropic glutamate receptor (mGluR) subtypes. Accordingly, the compounds of the present invention are expected to be useful in the treatment of conditions associated with excitatory activation of mGluR5 and for inhibiting neuronal damage caused by excitatory activation of mGluR5. The compounds may be used to produce an inhibitory effect of mGluR5 in mammals, including man.

The mGluR Group I receptor including mGluR5 are highly expressed in the central and peripheral nervous system and in other tissues. Thus, it is expected that the compounds of the invention are well suited for the treatment of mGluR5-mediated disorders such as acute and chronic neurological and psychiatric disorders, gastrointestinal disorders, and chronic and acute pain disorders.

The invention relates to compounds of Formula I, as defined hereinbefore, for use in therapy.

The invention relates to compounds of Formula I, as defined hereinbefore, for use in treatment of mGluR5-mediated disorders.

The invention relates to compounds of Formula I, as defined hereinbefore, for use in treatment of Alzheimer's disease senile dementia, AIDS-induced dementia, Parkinson's disease, amylotropic lateral sclerosis, Huntington's Chorea, migraine, epilepsy, schizophrenia, depression, anxiety, acute anxiety, ophthalmological disorders such as retinopathies, diabetic retinopathies, glaucoma, auditory neuropathic disorders such as tinnitus, chemotherapy induced neuropathies, post-herpetic neuralgia and trigeminal neuralgia, tolerance, dependency, Fragile X, autism, mental retardation, schizophrenia and Down's Syndrome.

The invention relates to compounds of Formula I, as defined hereinbefore, for use in treatment of pain related to migraine, inflammatory pain, neuropathic pain disorders such as diabetic neuropathies, arthritis and rheumatoid diseases, low back pain, post-operative pain and pain associated with various conditions including angina, renal or biliary colic, menstruation, migraine and gout.

The invention relates to compounds of Formula I as defined hereinbefore, for use in treatment of stroke, head trauma, anoxic and ischemic injuries, hypoglycemia, cardiovascular diseases and epilepsy.

A further aspect of the invention is the use of a compound according to formula I for the manufacture of a medicament for the treatment or prevention of obesity and obesity related conditions, as well as treating eating disorders by inhibition of excessive food intake and the resulting obesity and complications associated therewith.

The present invention relates also to the use of a compound of Formula I as defined hereinbefore, in the manufacture of a medicament for the treatment of mGluR Group I receptor-mediated disorders and any disorder listed above.

One embodiment of the invention relates to the use of a compound according to Formula I in the treatment of gastrointestinal disorders.

Another embodiment of the invention relates to the use of a compound according to Formula I, for the manufacture of a medicament for the inhibition of transient lower esophageal sphincter relaxations, for the treatment of GERD, for the prevention of G.I. reflux, for the treatment regurgitation, treatment of asthma, treatment of laryngitis, treatment of lung disease and for the management of failure to thrive.

A further embodiment of the invention relates to the use of a compound according to Formula I for the manufacture of a medicament for the treatment or prevention of functional gastrointestinal disorders, such as functional dyspepsia (FD). Yet another aspect of the invention is the use of a compound according to Formula I for the manufacture of a medicament for the treatment or prevention of irritable bowel syndrome (IBS), such as constipation predominant IBS, diarrhea predominant IBS or alternating bowel movement predominant IBS.

The invention also provides a method of treatment of mGluR5-mediated disorders and any disorder listed above, in a patient suffering from, or at risk of, said condition, which comprises administering to the patient an effective amount of a compound of Formula I, as hereinbefore defined.

The dose required for the therapeutic or preventive treatment of a particular disorder will necessarily be varied depending on the host treated, the route of administration and the severity of the illness being treated.

In the context of the present specification, the term "therapy" and "treatment" includes prevention or prophylaxis, unless there are specific indications to the contrary. The terms "therapeutic" and "therapeutically" should be construed accordingly. In this specification, unless stated otherwise, the term "antagonist" and "inhibitor" shall mean a compound that by any means, partly or completely, blocks the transduction pathway leading to the production of a response by the ligand. The term "disorder", unless stated otherwise, means any condition and disease associated with metabotropic glutamate receptor activity.

Non-Medical Use

In addition to their use in therapeutic medicine, the compounds of Formula I, salts or hydrates thereof, are also useful as pharmacological tools in the development and standardization of in vitro and in vivo test systems for the evaluation of the effects of inhibitors of mGluR related activity in laboratory animals such as cats, dogs, rabbits, monkeys, rats and mice, as part of the search for new therapeutics agents.

Methods of Preparation

Another aspect of the present invention provides processes for preparing compounds of Formula I, or salts or hydrates thereof. Processes for the preparation of the compounds in the present invention are described herein.

Throughout the following description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis. Examples of transformations are given below, and it is to be understood that the described transformations are not limited only to the generic groups or substituents for which the transformations are exemplified. References and descriptions on other suitable transformations are given in "Comprehensive Organic Transformations—A Guide to Functional Group Preparations" R. C. Larock, VHC Publishers, Inc. (1989).

References and descriptions of other suitable reactions are described in textbooks of organic chemistry, for example, "Advanced Organic Chemistry", March, 4th ed. McGraw Hill (1992) or, "Organic Synthesis", Smith, McGraw Hill, (1994). Techniques for purification of intermediates and final products include for example, straight and reversed phase chromatography on column or rotating plate, recrystallization, distillation and liquid-liquid or solid-liquid extraction, which will be readily understood by the one skilled in the art. The definitions of substituents and groups are as in formula I except where defined differently. The term "room temperature" and "ambient temperature" shall mean, unless otherwise specified, a temperature between 16 and 25° C.

The term "reflux" shall mean, unless otherwise stated, in reference to an employed solvent a temperature at or above the boiling point of named solvent.

| Abbreviations | |
|---|---|
| aq. | Aqueous |
| atm | atmosphere |
| BINAP | 2,2'Bis(diphenylphosphino)-1,1'-binaphthyl |
| Boc, BOC | tert-butoxycarbonyl |
| CDI | N,N'-Carbonyldiimidazole |
| dba | Dibenzylideneacetone |
| DCC | N,N-Dicyclohexylcarbodiimide |
| DCM | Dichloromethane |
| DEA | N,N-Diisopropylethylamine |
| DIBAL-H | Diisobutylaluminum hydride |
| DIC | N,N'-Diisopropylcarbodiimide |
| DMAP | N,N-Dimethyl-4-aminopyridine |
| DMF | Dimethylformamide |
| DMSO | Dimethylsulfoxide |
| DPPF | 1,1'-Bis(diphenylphosphino)ferrocene |
| EA or EtOAc | Ethyl acetate |
| EDC, EDCl | N-[3-(dimethylamino)propyl]-N'-ethylcarbodiimide hydrochloride |
| Et | Ethyl |
| Et$_2$O | Diethyl ether |
| EtI | Iodoethane |
| EtOH | Ethanol |
| Et$_3$N | Triethylamine |
| Fmoc, FMOC | 9-Fluorenylmethoxycarbonyl |
| h | hour(s) |
| HBTU | O-(Benzotriazol-1-yl)-N,N,N',N'-tetramethyluronium hexafluorophosphate |
| Hep | heptane |
| Hex | hexane(s) |
| HetAr | Heteroaryl |
| HOBt | N-Hydroxybenzotriazole |
| HPLC | high performance liquid chromatography |
| LAH | lithium aluminum hydride |
| LCMS | HPLC mass spec |
| MCPBA | m-chlorbenzoic acid |
| Me | Methyl |
| MeCN | Acetonitrile |
| MeI | Iodomethane |
| MeMgCl | methyl magnesium chloride |
| MeOH | Methanol |
| min | Minutes |
| NaOAc | sodium acetate |
| nBu | normal butyl |
| nBuLi, n-BuLi | 1-butyllithium |
| NCS | N-chlorosuccinimide |
| NMR | nuclear magnetic resonance |
| o.n. | over night |
| OAc | acetate |
| OMs | mesylate or methane sulfonate ester |
| OTs | tosylate, toluene sulfonate or 4-methyl-benzene sulfonate ester |
| PPTS | pyridinium p-toluenesulfonate |
| pTsOH | p-toluenesulfonic acid |
| RT, rt, r.t. | room temperature |
| sat. | Saturated |
| SPE | solid phase extraction |
| TBAF | tetrabutylammonium fluoride |
| tBu, t-Bu | tert-butyl |
| tBuOH, t-BuOH | tert-butanol |
| TEA | Triethylamine |
| THF | Tetrahydrofuran |

Preparation of Intermediates

The compounds, and the corresponding intermediates throughout the non-limiting synthetic paths for which preparations are given below, are useful for further preparation of compounds of formula I or may represent the same. Other starting materials are either commercially available or can be prepared via methods described in the literature.

[1,2,4]Triazolethiones and Alkylsulphonyl[1,2,4]triazoles

Scheme 1a

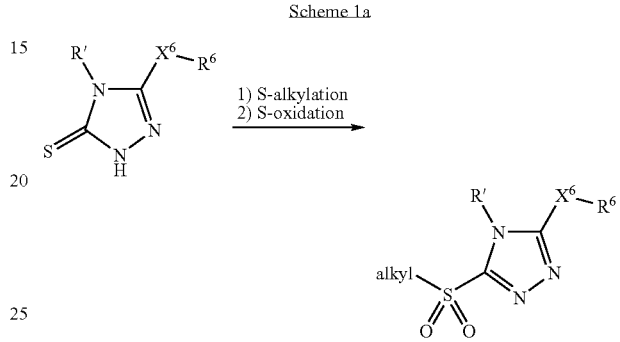

With reference to scheme 1a, alkylsulphonyl[1,2,4]triazoles can be prepared from the corresponding [1,2,4]triazolethiones by initial alkylation of the sulphur atom with primary alkyl halides such as MeI and EtI (alkyl is Me and Et respectively) in MeOH, EtOH, THF, acetone or the like at −30 to 100° C., followed by oxidation of the sulphur atom using for example KMnO$_4$ in mixtures of water and acetic acid, or mCPBA in DCM, at −20 to 120° C., or by using any other suitable oxidant.

Scheme 1b

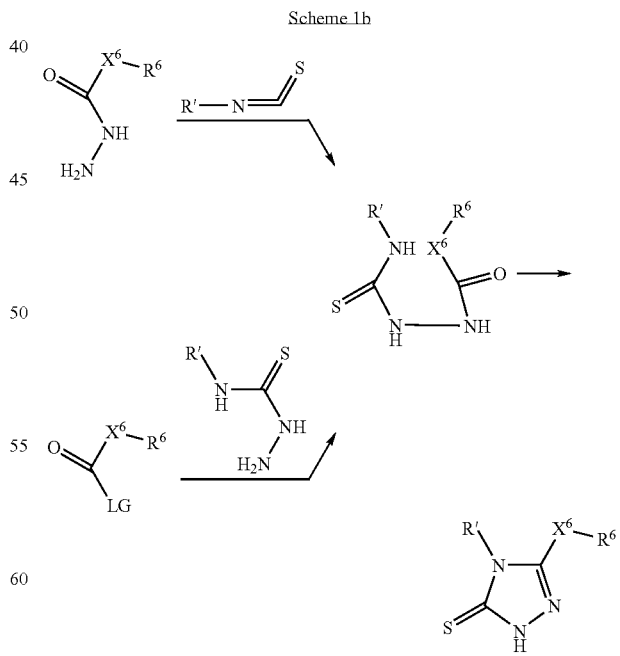

In reference to scheme 1b, [1,2,4]triazolethiones, wherein R' is a suitable side chain which may or may not be protected as appropriate, are for example prepared by N-acylation of a thiosemicarbazide, using any suitable acylating agent such as acid chlorides, bromides or fluorides (LG is Cl, Br or F) in for example pyridine, or acids (LG is OH), that are activated by the treatment with standard activating reagents as described herein below, in DMF, THF, DCM or the like at −20 to 120° C., followed by ring closure of the initially formed acyclic intermediate either spontaneously under the conditions of the acylation, or by heating at 50 to 150° C. in pyridine or in aqueous solvents in the presence of a base, such as NaHCO$_3$ or Na$_2$CO$_3$, with or without co-solvents such as dioxane, THF, MeOH, EtOH or DMF. This acyclic intermediate can also be formed by treatment of the proper acyl hydrazide with a suitable isothiocyanate in for example 2-propanol, DCM, THF or the like at −20 to 120° C.

[1,2,4]oxadiazoles

Scheme 2

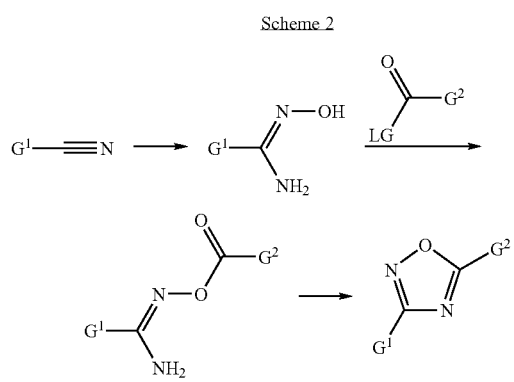

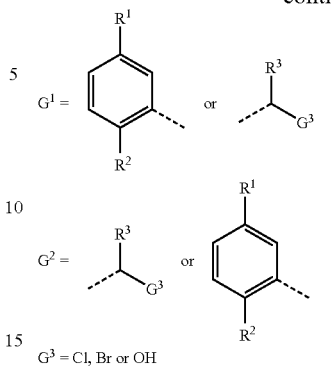

$G^3$ = Cl, Br or OH

With reference to scheme 2, [1,2,4]oxadiazoles with a carbon alpha to the heterocycle, wherein $G^1$, $G^2$ and $G^3$ are defined as described in scheme 2, are formed by cyclization of $G^1$- and $G^2$-substituted-acyloxyimidamides in solvents such as pyridine, DMF, or water containing mixtures thereof, at 40 to 140° C., alternatively in aqueous alcoholic solvents in the presence of sodium acetate at temperatures from 40 to 140° C., with the later method being preferred if one of the groups $G^1$ or $G^2$ contains a chiral stereocenter. Acyloxyimidamides are formed by coupling with a proper acylating agent carrying a leaving group LG with a $G^1$-substituted hydroxamidine. The leaving group LG may be chloro or any other suitable leaving group as for example generated by in situ treatment of the corresponding acid (LG is OH) with standard activating reagents as described herein below. $G^1$-substituted hydroxamidines are formed by reaction of the corresponding nitrile with the free base of hydroxylamine, or hydroxylamine hydrochloride in the presence of a base such as triethylamine, pyridine or sodium carbonate, in solvents such as ethanol, water or pyridine at temperatures from −20 to 120° C.

Cyclic amino[1,2,4]triazoles

Scheme 3

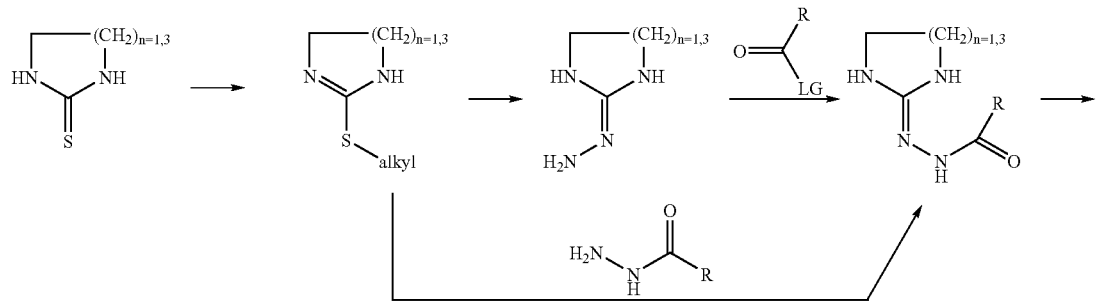

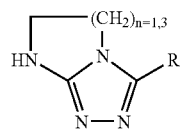

With reference to scheme 3, cyclic amino[1,2,4]triazoles, wherein R is $X^6$—$R^3$ as defined in formula I, are obtained by treating cyclic carbono-2-one hydrazones (e.g. 1,3-diazepan-2-one hydrazone for n=3 or the likes) with a proper acylating agent carrying a leaving group LG in suitable solvent such as THF, pyridine or DMF at −20 to 100° C. The reaction initially leads to an open intermediate that either forms a triazole ring spontaneously, or can be made to do so by conventional, or microwave assisted, heating at 50 to 200° C. in for example pyridine or DMF. The leaving group LG may be chloro, bromo or fluoro (LG is Cl, Br or F), the corresponding anhydride (LG is O—C(═O)R) or any other suitable leaving group as for example generated by in situ treatment of the corresponding acid (LG is OH) with standard activating reagents as described herein above. Cyclic carbono-2-one hydrazones may be generated from isothioureas, in which the S-alkyl (for example S-Me or S-Et) moiety acts as a leaving group upon treatment with hydrazine in solvents such as pyridine, methanol, ethanol, 2-propanol, THF or the like at −20 to 180° C. The open intermediate can also be directly generated by treatment of isothioureas with acyl hydrazides under the same conditions as described for the reaction with hydrazine. Cyclic isothioureas are obtained by S-alkylation of the corresponding thioureas, which are commercially available or prepared according to standard procedures as known to the one skilled in the art, with for example MeI or EtI in acetone, EtOH, THF, DCM or the like at −100 to 100° C.

prepared from their corresponding lactams by treatment with $Me_3OBF_4$ or dimethylsulfate [Org. Prep. Proced. Int; 24, 1992, pp. 147-158 or Tetrahedron Lett. 42, 2001, pp. 173-1776]. R-substituted lactams are either commercially available or may be prepared by alkylation in the alpha position by treatment with 2 equivalents of a strong base such as n-BuLi followed by addition of 1 equivalent of alkylating agent, such as alkyl halide, mesylate or triflate, in an aprotic solvents such as THF [J. Org. Chem. 64, 1999, pp. 6041-6048] or, alternatively, via a N-protected lactam, e.g. trimethylsilyl valerolactam or the likes, where only one equivalent of base is needed to generate the anion for alkylation [J. Org. Chem. 65, 2000, pp. 2684-2695]. The alkylation results in the formation of racemic product which may be separated into its enantiopure forms here, or at a later stage of the synthetic pathway by e.g. chiral chromatography.

2-Aryl-2H-[1,2,3]triazole-4-carbaldehydes

Scheme 5

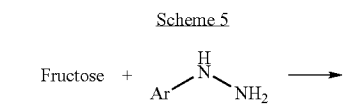

Carbocylic[1,2,4]triazoles

Scheme 4

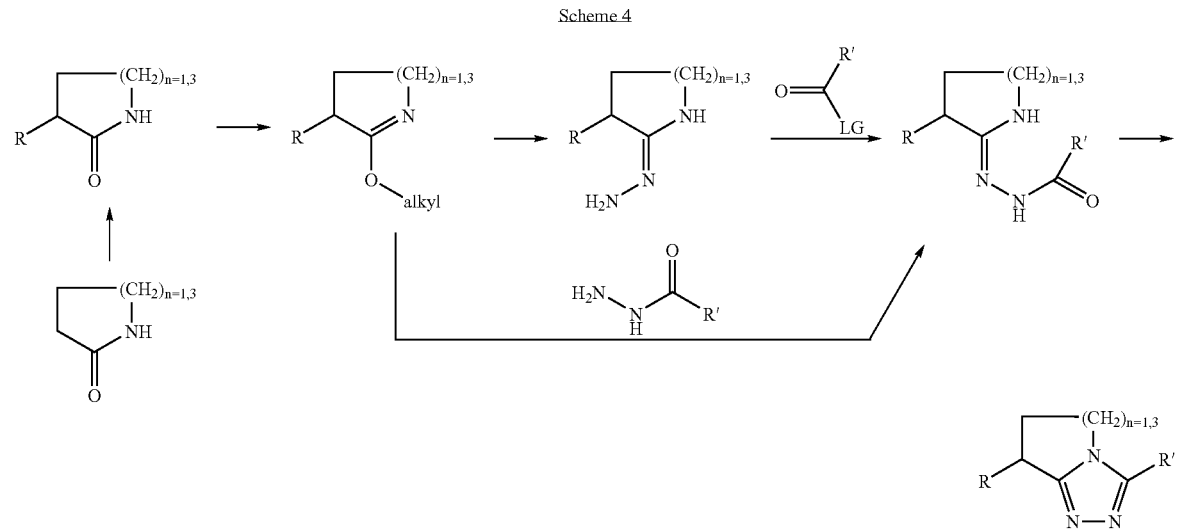

With reference to scheme 4, wherein R either is H, or alkyl (Me, Et) and R' is $X^6$—$R^3$ as defined in formula I, carbocylic [1,2,4]triazoles are obtained by treating cyclic lactam hydrazones with a proper acylating agent to lead to an open chain intermediate which forms the triazole ring spontaneously or by heating as described herein above. Such cyclic lactam hydrazones are generated from the cyclic enol ether, in which the O-alkyl (alkyl is Me) moiety acts as a leaving group upon treatment with hydrazine as described herein above. Such open chain intermediates may also be formed directly by treatment of lactam enol ethers by treatment with acyl hydrazides as described herein above. Lactam enol ethers are -continued

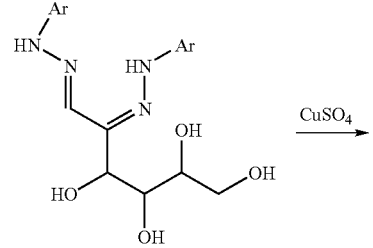

-continued

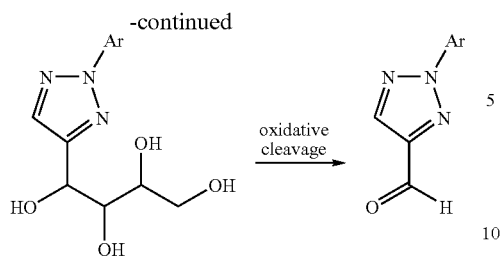

-continued

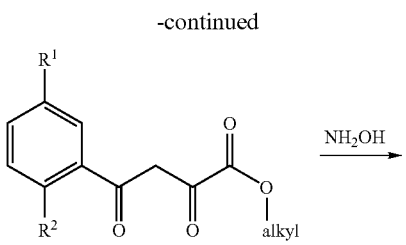

With reference to scheme 5, wherein Ar is 5-R$^1$,2-R$^2$-phenyl as defined in formula I, [1,2,3]triazole-4-carbaldehydes may be obtained from aryl glucosetriazoles by oxidative cleavage, employing for example periodic acid in aqueous mixtures of dioxane or THF at −20 to 120° C. Aryl glucosetriazoles may be obtained by cyclization of the intermediate aryl glucosazone in the presence of copper (II) sulfate in aqueous mixtures of for example dioxane or THF at −20 to 120° C. The aryl glucosazone in turn is made by coupling of arylhydrazines with fructose in acetic acid and water at −20 to 120° C. [Buckler, R.; Hartzler, H.; Kurchacova, E.; Nichols, G.; Phillips, B.; J. Med. Chem.; 1978; 21(12); 1254-1260, and Riebsomer, J.; Sumrell, G.; J. Org. Chem.; 1948; 13(6); 807-814]

In reference to scheme 6, isoxazoles are formed by reaction and in-situ cyclization of dioxo butyric ester derivatives with hydroxylamine hydrochloride in solvents such as ethanol, 2-propanol or DMF at temperatures from 40 to 140° C. Dioxo butyric esters are formed through the reaction of acetophenones with dialkyl oxolates (alkyl is for example Me or Et) in the presence of a strong base such as sodium hydride in solvents such as DMF or toluene at temperatures from −20 to 120° C.

Isoxazole-5-carboxylic acid esters

Scheme 6

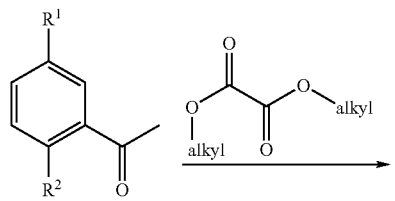

[1, 3, 4]oxadiazoles

Scheme 7

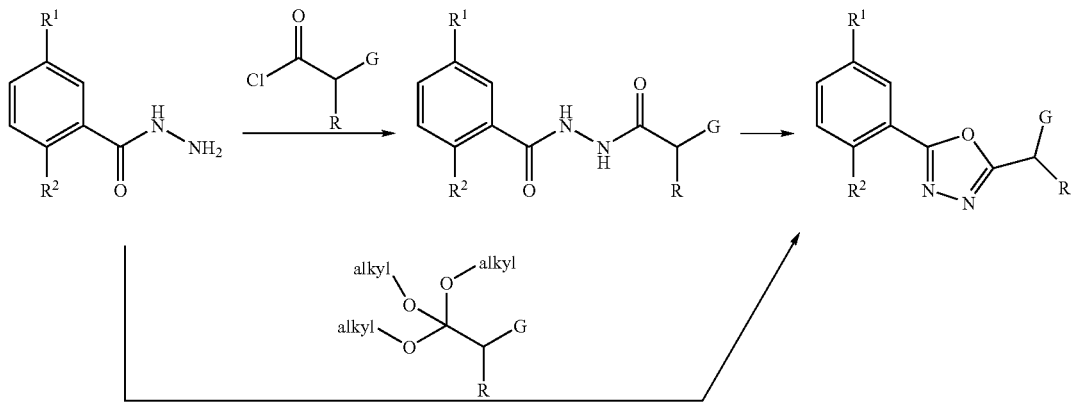

G = Cl or Br

With reference to scheme 7, wherein R is H or alkyl (Me, Et), starting from acid hydrazides, coupling with an aliphatic acid chloride derivative in THF, DMF, toluene or the like, optionally in the presence of a base such as triethylamine or a carbonate, leads to the formation of an acyl benzohydrazide derivative, which is cyclized at elevated temperatures in the presence of a dehydrating agent such as phosphorous pentoxide in solvents such as toluene or DMF or mixtures thereof to yield the [1,3,4]oxadiazole product. Alternatively, [1,3,4]oxadiazoles may be made directly from the acid hydrazide using trialkyl ortho esters either neat or in solvents such as toluene or xylenes at elevated temperatures.

Triazole ethers

Scheme 8

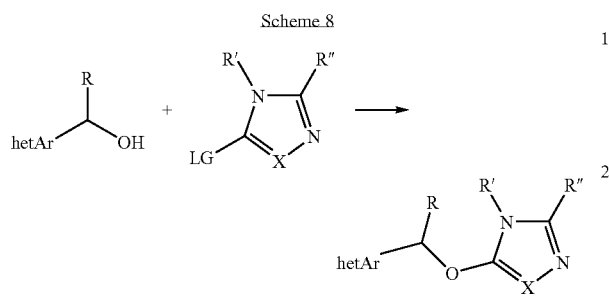

With reference to scheme 8, wherein R is H or alkyl (Me, Et), R' is a suitable side chain which may or may not be protected as appropriate, and R'' is $X^6$—$R^3$ as defined in formula I, oxygen linked triazoles may be prepared by bond formation through nucleophilic replacement of a leaving group (LG) in which an alcohol acts as O-nucleophile under basic conditions. A base is used, for example, NaH or $Cs_2CO_3$, at temperatures from 0 to 80° C. in polar aprotic solvents such as DMF or acetonitrile. Examples of suitable leaving groups are alkylsulfonyls, such as methanesulfonyl and ethanesulfonyl, and halogens, such as chloro.

Arylhydrazones and Arylsulfonylhydrazones

Scheme 9

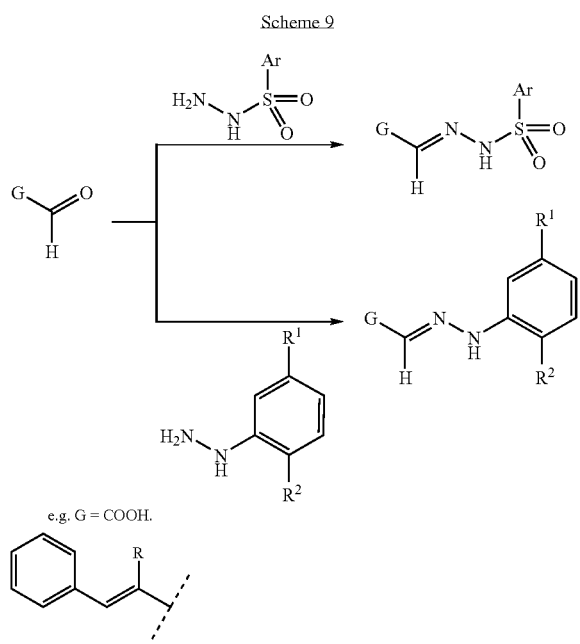

e.g. G = COOH.

In reference to scheme 9, arylsulfonylhydrazones are prepared through condensation between aldehydes, for example cinnamaldehyde or glyoxalic acid, with arylsulphonylhydrazines, such as 4-toluensulfonylhydrazine, in a suitable solvent, for example methanol, ethanol, DMF or dialkylethers, at a temperature between 0 to 100° C., alternatively without solvent under microwave irradiation. Similarly, arylhydrazones may be formed from the reaction of arylhydrazines, with aldehydes. [J. Med. Chem. 1980, 23, 631-634; Monatshefte fuer Chemie 2001, 403-406; J. Med. Chem. 2000, 43, 953-970; J. Med Chem. 1978, 21, 1254-60]

Tretrazole formation

Scheme 10a

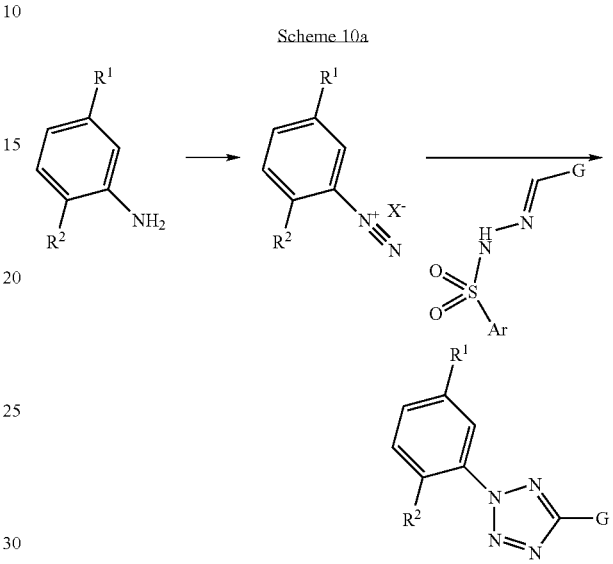

In reference to scheme 10a, tetrazoles, wherein G is an electron withdrawing group, such as an olefin, carbonyl or aryl group, may be prepared by 1,3-dipolar cycloaddition of a diazonium salt onto an aryl sulfonyl hydrazone followed by elimination of the arylsulfinic acid to generate the tetrazole ring, in protic solvents such as water and alcohol or mixtures thereof, in basic aprotic solvents such as pyridine, or mixtures of these solvents with protic solvents used to generate the diazonium salt. [J. Med. Chem. 2000, 43, 953-970]. Diazonium salts in turn are available from a suitably substituted aryl or heteroaryl amine using well known methods, via diazotization using a nitrite source such as sodium nitrite or isoamyl nitrite in the presence of a suitable acid source such as hydrochloric acid or tetrafluoroboric acid in a solvent such as water at a temperature between −10 to 0° C. In the case where a less soluble counterion X⁻ is employed, such as tetrafluoroborate, the diazonium salt thus formed may be collected by precipitation and used in subsequent reactions under non-aqueous conditions. Soluble diazonium salts formed using other acid sources may be precipitated by the addition of a suitable reagent such as tetrafluoroboric acid or sodium tetrafluoroborate.

Scheme 10b

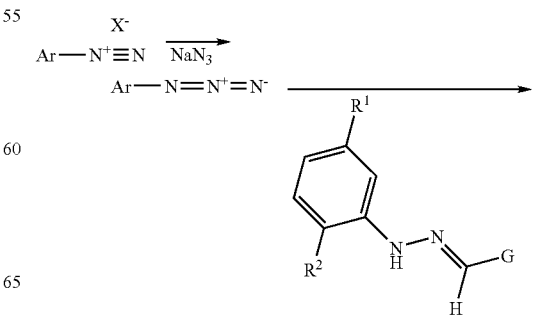

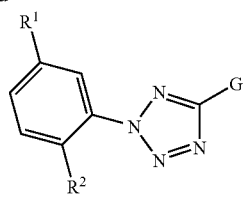

In reference to scheme 10b, tetrazoles may also be prepared from the reaction of an arylhydrazone, wherein G is defined as in scheme 9 and 10, with an aryl azide in a suitable solvent such as ethanol or pyridine. [J. Med Chem. 1978, 21, 1254-60] Aryl azides may be formed for example by using sodium azide with an aryl diazonium salt, which may in turn be prepared as described above from an aryl amine, for example aniline or 2,4,6-tribromoaniline. The aryl azide may be considered as a nitrogen transfer reagent since cycloaddition onto the hydrazone is followed by elimination to regenerate the aryl amine precursor to the diazonium salt.

Preparation of 2-aryl tetrazole 5-carbonyls

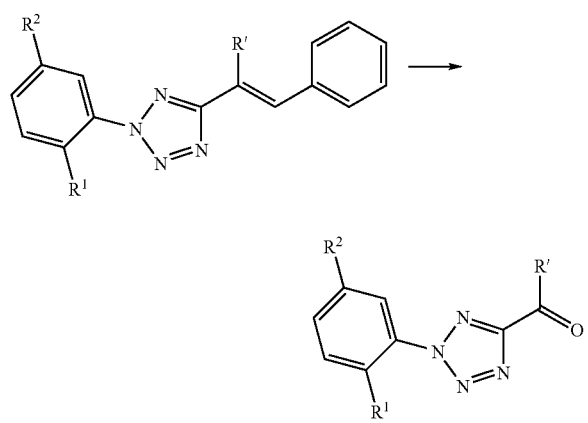

Typically, G, as in reference to scheme 10a and 10b, is a group which may be employed as a precursor to the $X^6$ moiety in compounds of formula I, such as an olefin or carboxylic acid or acid derivative. With reference to scheme 11, when G is an aryl olefin, derived for example from cinnamaldehyde where R is H, the olefin group can be cleaved to provide an aldehyde directly in a one-pot process using a reagent such as ozone or via the diol using a dihydroxylation reagent such as osmium tetroxide as known by the one skilled in the art followed by subsequent cleavage using a reagent such as lead (IV) acetate. When a substituted cinnamaldehyde, such as α-methylcinnamaldehyde wherein R" is methyl, is employed, a ketone would result from the cleavage of the olefin. [J. Med. Chem. 2000, 43, 953-970].

Functional group transformations

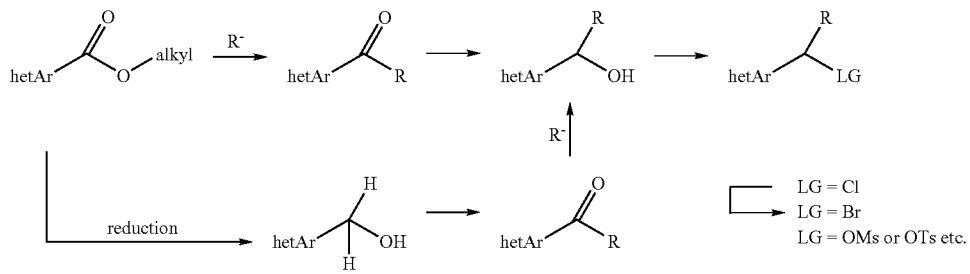

With reference to scheme 12, aliphatic alcohols may for example be converted by standard methods to the corresponding halides by the use of for example triphenylphosphine in combination with either iodine, N-bromosuccinimide or N-chlorosuccinimide, or alternatively by treatment with tribromophosphine or thionyl chloride. Alcohols may be transformed to other leaving groups such as mesylates or tosylates by employing the appropriate sulfonyl halide or sulfonyl anhydride in the presence of a non-nucleophilic base together with the alcohol to obtain the corresponding sulphonates. Chlorides or sulphonates may be converted to the corresponding bromides or iodides by treatment with bromide salts, for example LiBr, or iodide salts, such as LiI. Further standard methods to obtain alcohols include the reduction of the corresponding carbonyl containing groups such as methyl or ethyl esters, aldehydes or ketones, by employing common reducing agents such as boranes, lithium borohydride, lithium aluminium hydride, or hydrogen in the presence of a transition metal catalyst such as complexes of for example ruthenium or iridium, or alternatively palladium on charcoal. Ketones and secondary alcohols may be obtained by treatment of carboxylic acid esters and aldehydes respectively, with the appropriate carbon nucleophile, such as alkyl-Grignard reagents or alkyl-lithium reagents according to standard protocols. Heteroaromatic aldehydes may be prepared from the corresponding primary alcohols by oxidation procedures well known to the one skilled in the art, such as the employment of $MnO_2$ as oxidant, or by Swern oxidation.

Preparation of Final Compounds

The subsequent described non-limiting methods of preparation of final compounds are illustrated and exemplified by drawings in which the generic groups, or other structural elements of the intermediates correspond to those of formula I. It is to be understood that an intermediate containing any other generic group or structural element than those of formula I can be used in the exemplified reactions, provided that this group or element does not hinder the reaction and that it can be chemically converted to the corresponding group or element of formula I at a later stage which is known to the one skilled in the art.

By nucleophilic intermolecular displacement

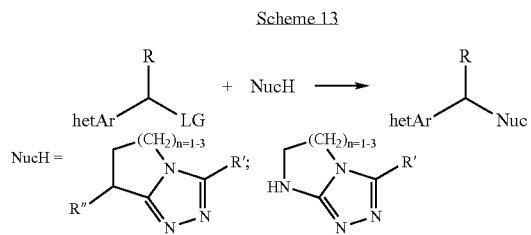

Scheme 13

With reference to scheme 13, wherein R" is H or alkyl (Me, Et), R is H or alkyl (Me, Et) and R' is $X^6$–$R^3$ as defined in formula I, compounds of formula I can for example be prepared by bond formation through nucleophilic displacement of a leaving group (LG) in which the nucleophilic atom might be the amino-nitrogen atom of a heterocyclic amine, the alpha-carbon of an alkyl substituted heteroaromatic ring.

Amino-nitrogen atoms of heterocyclic amines, and the alpha-carbons of alkyl substituted heteroaromatics, are generally not reactive in the neutral protonated form and are therefore preferably fully or partly converted to more nucleophilic anionic forms by treatment with bases in suitable solvents such as LDA, HMDS-alkali, or n-BuLi in THF, diethylether or toluene, or NaH in for example DMF, or $K_2CO_3$ or $Cs_2CO_3$ in acetonitrile or ketones such as 2-butanone, either in situ or just before the reaction with a suitable electrophile carrying a leaving group at a temperature from —100 to 150° C. The nitrogen atoms of secondary aliphatic amines are generally nucleophilic enough to displace a leaving group in the corresponding neutral forms, but preferably a base such as $K_2CO_3$, $Cs_2CO_3$, TEA, DEA or the like is added to facilitate the reaction in solvents such as acetonitrile, DMF or DCM at 0 to 150° C. For carbon nucleophiles, the leaving group is preferably bromo, for nitrogen nucleophiles examples of suitable leaving groups LG include chloro, bromo, OMs and OTs. Optionally, catalytic or stoichiometric amounts of an alkali metal iodide, such as LiI, can be present in the reaction to facilitate the same through in situ displacement of the leaving group to iodo.

By nucleophilic intramolecular displacement

Scheme 14

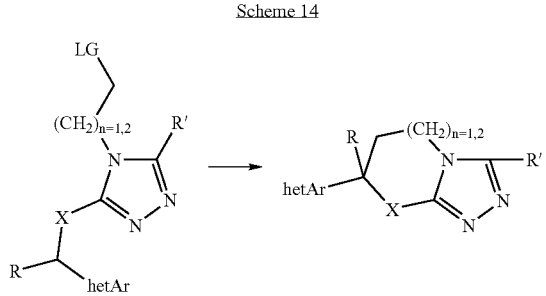

With reference to scheme 14, wherein R is H or alkyl (Me, Et) and X is either S or O, compounds of formula I can for example be prepared by intramolecular bond formation through nucleophilic displacement of a leaving group (LG) in which the nucleophilic atom might be the alpha-carbon of an alkyl substituted heteroaromate under conditions as described herein above for intermolecular displacements where preferred bases are for example LDA, HMDS-alkali, or NaH as described herein above.

Preparation of fused Piperazine-triazoles

Scheme 15a

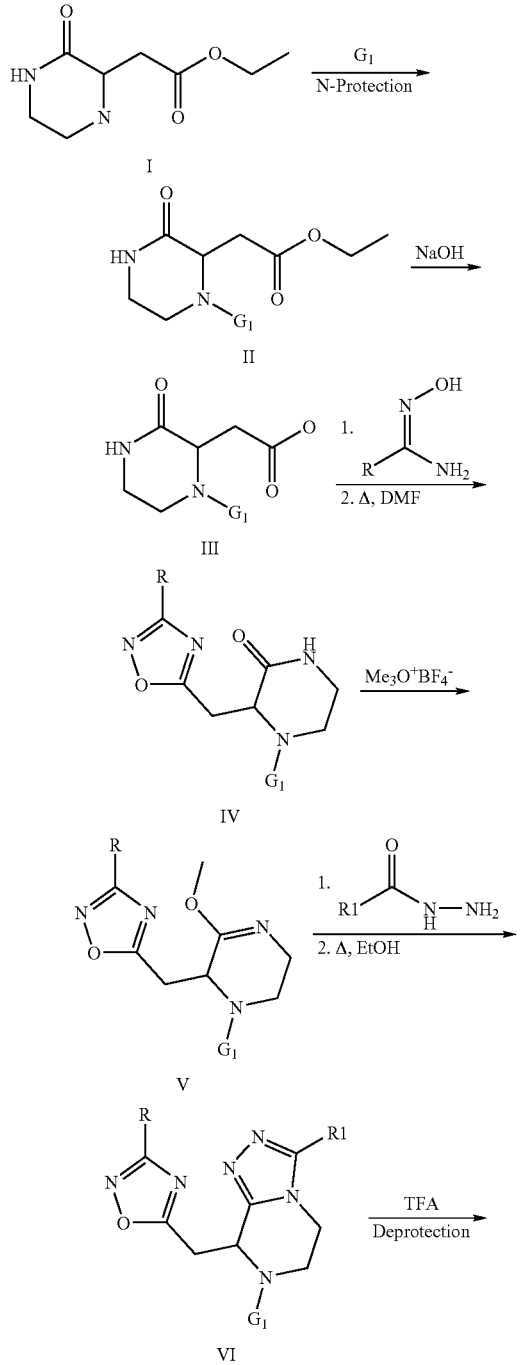

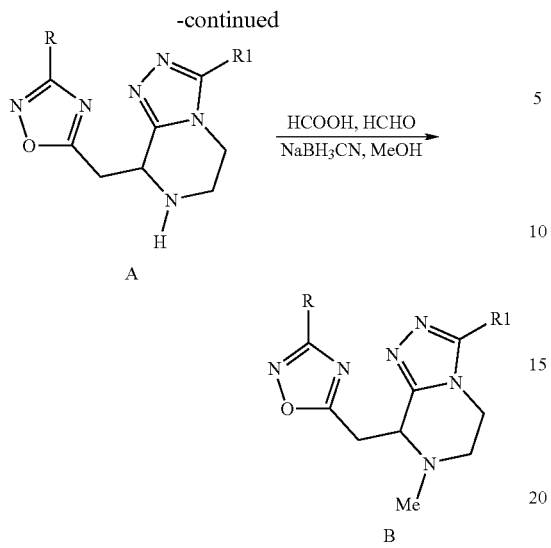

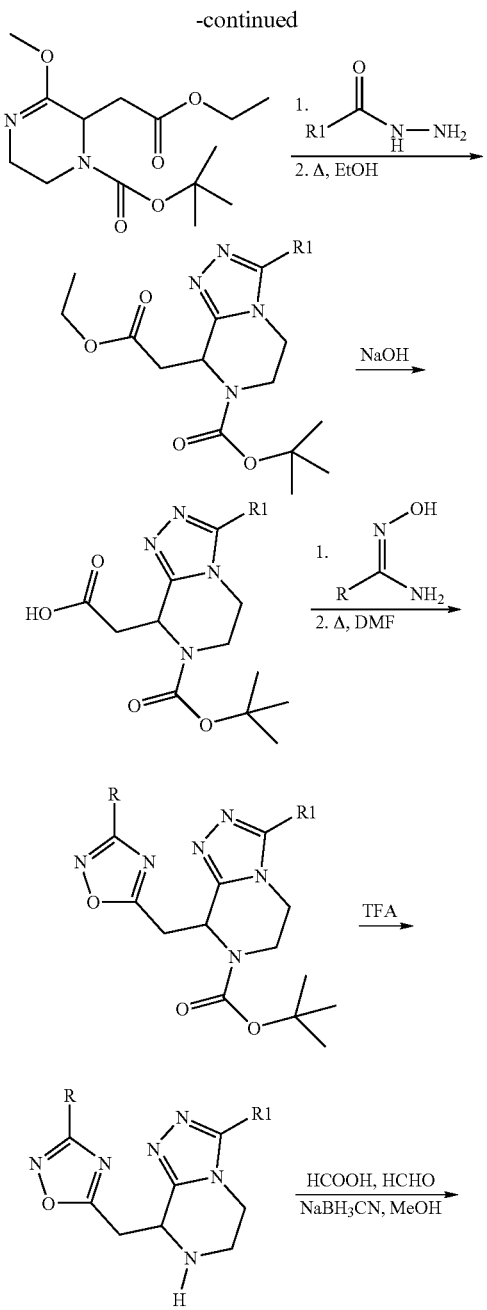

With reference to scheme 15a, the triazolopiperazines can be prepared from the piperazinone derivative by initial N-protection to give intermediate II. The intermediate can then be hydrolyzed to the acid III. The corresponding 1,2,4-oxadiazole IV can then be generated as described above. The triazolopiperazine intermediate VI can then be obtained by first converting IV to the cyclic imidoate, with a reagent such as Me$_3$O$^+$BF$_4^-$ or dimethyl sulfate (ref: a) Sheu, Jennline; Smith, Michael B.; Oeschger, Thomas R.; Satchell, Jacqueline; Org. Prep. Proced. Int.; 24; 2; 1992; 147-158; b) Hutchinson, Ian S.; Matlin, Stephen A.; Mete, Antonio, Tetrahedron Lett.; 42; 9; 2001; 1773-1776). The alkoxy group can then be displaced by a acyl hydrazide (or hydrazine with an acylating agent as described in Scheme 4) followed by a ring closing condensation to form the triazole heterocycle. This can be done in ethanol, toluene, DMF or pyridine under thermal conditions with regular heating or microwave irradiation (ref: Lawson, Edward C.; Hoekstra, William J.; Addo, Michael F.; Andrade-Gordon, Patricia; Damiano, Bruce P.; Kauffman, Jack A.; Mitchell, John A.; Maryanoff, Bruce E.; Bioorg. Med. Chem. Lett.; EN; 11; 19; 2001; 2619-2622). The protecting group can then be removed to afford compounds of formula A. Compound A can then be subjected to reductive alkylation to deliver compounds of formula B. Alternatively, compounds of formula A and B also be obtained according to the reaction sequence illustrated in Scheme 15b as shown below.

Scheme 15b

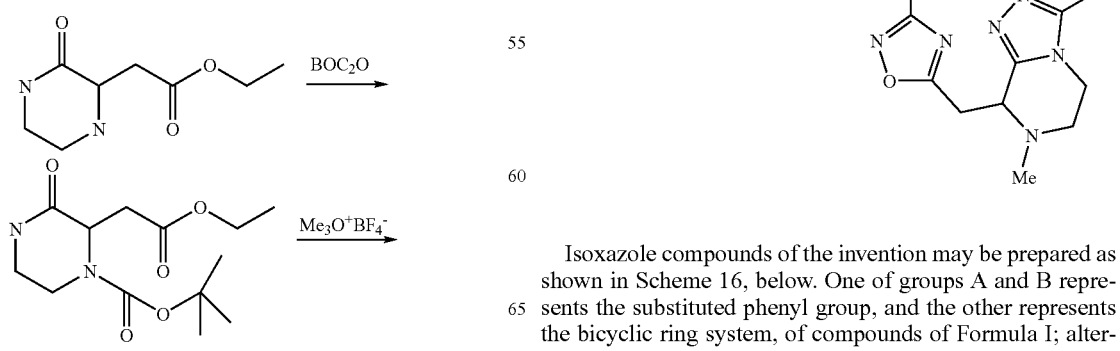

Isoxazole compounds of the invention may be prepared as shown in Scheme 16, below. One of groups A and B represents the substituted phenyl group, and the other represents the bicyclic ring system, of compounds of Formula I; alternatively, A and B represent precursors of those groups:

Scheme 16

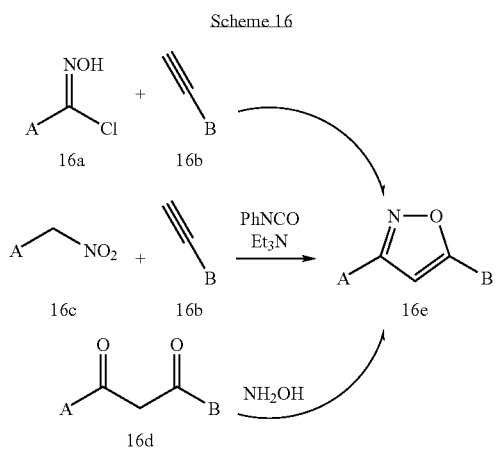

In more detail, compounds of formula 16e may be prepared by a 1,3-dipolar cycloaddition between compounds of formula 16a and 16b under basic conditions, using a suitable base such as sodium bicarbonate or triethylamine at suitable temperatures (0° C.-100° C.) in solvents such as toluene. Synthesis of compounds of type 16a has previously been described in the literature, e.g. Kim, Jae Nyoung; Ryu, Eung K; J. Org. Chem. (1992), 57, 6649-50. 1,3-Dipolar cycloaddition with acetylenes of type 16b can also be effected using substituted nitromethanes of type 16c via activation with an electrophilic reagent such as PhNCO in the presence of a base such as triethylamine at elevated temperatures (50-100° C.). Li, C-S.; Lacasse, E.; Tetrahedron Lett. (2002) 43; 3565-3568. Several compounds of type 16c are commercially available, or may be synthesized by standard methods known by one skilled in the art.

Alternatively, compounds of formula 16d, which are available via a Claisen condensation of a methyl ketone and an ester using basic conditions using such bases as sodium hydride or potassium tert-butoxide, may yield compounds of formula 16e via condensation and subsequent cyclization using hydroxylamine, for example in the form of the hydrochloric acid salt, at elevated temperatures (60-120° C.).

It is understood that for both methods protection of intermediates and/or subsequent functional group transformations may be necessary, as will be appreciated by those skilled in the art. In the case of an ester group, these transformations may include, but is not limited to either of following three procedures: a) Complete reduction using a suitable reducing agent such as LAH in solvents such as THF. b) Partial reduction using a suitable selective reducing agent such as DIBAL followed by alkylation with an alkyl halide. c) Alkylation using an alkylmetal reagent such as an alkyl magnesium halide in solvents such as toluene or THF, followed by reduction with for example sodium borohydride in methanol.

The invention will now be illustrated by the following non-limiting examples.

General Methods

All starting materials are commercially available or earlier described in the literature. The $^1$H and $^{13}$C NMR spectra were recorded either on Bruker 300, Bruker DPX400 or Varian +400 spectrometers operating at 300, 400 and 400 MHz for $^1$H NMR respectively, using TMS or the residual solvent signal as reference, in deuterated chloroform as solvent unless otherwise indicated. All reported chemical shifts are in ppm on the delta-scale, and the fine splitting of the signals as appearing in the recordings (s: singlet, br s: broad singlet, d: doublet, t: triplet, q: quartet, m: multiplet). Analytical in line liquid chromatography separations followed by mass spectra detections, were recorded on a Waters LCMS consisting of an Alliance 2795 (LC) and a ZQ single quadropole mass spectrometer. The mass spectrometer was equipped with an electrospray ion source operated in a positive and/or negative ion mode. The ion spray voltage was ±3 kV and the mass spectrometer was scanned from m/z 100-700 at a scan time of 0.8 s. To the column, X-Terra MS, Waters, C8, 2.1×50 mm, 3.5 mm, was applied a linear gradient from 5% to 100% acetonitrile in 10 mM ammonium acetate (aq.), or in 0.1% TFA (aq.).

Preparative reversed phase chromatography was run on a Gilson autopreparative HPLC with a diode array detector using an XTerra MS C8, 19×300 mm, 7 mm as column.

Purification by a chromatotron was performed on rotating silica gel/gypsum (Merck, 60 PF-254 with calcium sulphate) coated glass sheets, with coating layer of 1, 2, or 4 mm using a TC Research 7924T chromatotron.

Purification of products were also done using Chem Elut Extraction Columns (Varian, cat #1219-8002), Mega BE-SI (Bond Elut Silica) SPE Columns (Varian, cat #12256018; 12256026; 12256034), or by flash chromatography in silica-filled glass columns.

Microwave heating was performed in a Smith Synthesizer Single-mode microwave cavity producing continuous irradiation at 2450 MHz (Personal Chemistry AB, Uppsala, Sweden).

Preparation of Intermediates

EXAMPLE 1

[3-(2-Thienyl)-5-thioxo-1,5-dihydro-4H-1,2,4-triazol-4-yl]acetic acid

Methyl N-(thioxomethylene)glycinate (2.06 g) and thiophene-2-carbohydrazide (2.57 g) in isopropanol (50 ml) was heated at 70° C. while stirring for 16 h. The mixture was allowed to come to r.t. and the formed precipitate collected and heated at reflux in 1.0 M aqueous NaHCO$_3$ solution for 2 h. After cooling to r.t. and acidification with conc. HCl (aq.) the product was extracted into EA, which was washed with brine and then dried over MgSO$_4$ before concentration to dryness to yield crude title compound which was used directly in the next step.

EXAMPLE 2

4-(2-Hydroxyethyl)-5-(2-thienyl)-2,4-dihydro-3H-1,2,4-triazole-3-thione

All of the crude [3-(2-thienyl)-5-thioxo-1,5-dihydro-4H-1,2,4-triazol-4-yl]acetic acid from the previous step was dissolved in THF (20 ml). This solution was added dropwise at 0° C. to a slurry of LAH (2 g) in THF (80 ml) while stirring before allowed to come to r.t. for 2 h. The r.m. was then quenched with sat. Na$_2$SO$_4$ (aq.) at 0° C. and the pH adjusted to 3-4 before filtration through celite. The THF was removed from the filtrate by concentration and the product extracted with EA from the remaining aq. mixture. The EA-phase was then washed with brine and dried over MgSO$_4$ before concentration to dryness to yield a crude material that was recrystallized from MeOH to provide 485 mg of the title compound. $^1$H NMR (DMSO-d6): 13.94 (br.s, 1H), 7.86 (d, 1H), 7.81 (d, 1H), 7.24 (dd, 1H), 5.09 (t, 1H), 4.16 (t, 2H), 3.76 (q, 2H)

EXAMPLE 3

2-[3-({[5-(5-Chloro-2-fluorophenyl)-1,2,4-oxadiazol-3-yl]methyl}thio)-5-(2-thienyl)-4H-1,2,4-triazol-4-yl]ethanol 4-(2-Hydroxyethyl)-5-(2-thienyl)-2,4-dihydro-3H-1,2,4-triazole-3-thione (101 mg), 5-(5-chloro-2-fluorophenyl)-3-(chloromethyl)-1,2,4-oxadiazole (116 mg), and potassium carbonate (86 mg) was stirred in a mixture of DMF (2 ml) and MeCN (15 ml) at r.t. for 3 h before concentration to dryness and washing of the residue with water, and then with EtOAc, to provide 122 mg of the title compound as a white solid.
$^1$H NMR (DMSO-d6): 8.04 (dd, 1H), 7.83 (m, 1H), 7.78 (d, 1H), 7.66 (d, 1H), 7.58 (t, 1H), 7.22 (dd, 1H), 5.16 (t, 1H), 4.59 (s, 2H), 4.18 (t, 2H), 3.64 (q, 2H)

EXAMPLE 4

2-[3-({[5-(5-Chloro-2-fluorophenyl)-1,2,4-oxadiazol-3-yl]methyl}thio)-5-(2-thienyl)-4H-1,2,4-triazol-4-yl]ethyl methanesulfonate To a solution of 2-[3-({[5-(5-chloro-2-fluorophenyl)-1,2,4-oxadiazol-3-yl]methyl}thio)-5-(2-thienyl)-4H-1,2,4-triazol-4-yl]ethanol in a mixture of DMF (1 ml) and pyridine (0.5 ml) was added methanesulfonyl chloride (20 uL). The mixture was stirred at r.t. for 24 h before poured onto water (10 ml). The crude product was filtered off and purified by chromatography on silica gel using 0-5% MeOH in DCM as eluent to give 43 mg of the title compound, which was used directly in the next step.

EXAMPLE 5 a) 3-pyridin-4-yl-6,7,8,9-tetrahydro-5H-[1,2,4]triazolo[4,3-α][1,3]diazepine

A mixture of 1,3-diazepan-2-one hydrazone hydroiodide (1.00 g, 3.9 mmol) and isonicotinoyl chloride hydrochloride (695 mg, 3.9 mmol) was heated in a microwave reactor at 160° C. for 10 min. The reaction mixture was poured into Na$_4$CO$_3$ solution, sat., and extracted with DCM. The organic phase was dried and concentrated. Flash chromatography (DCM/MeOH 20:1) gave 1.74 g crude title compound which was used directly in the next step. $^1$H NMR: 1.89 (s, 4H), 3.15 (m, 2H), 3.86 (m, 2H), 7.44 (d, 2H), 8.66 (d, 2H).

The following compounds were prepared in an analogous manner:

b) 3-(3,5-difluorophenyl)-6,7,8,9-tetrahydro-5H-[1,2,4]triazolo[4,3-a][1,3]diazepine 180 mg (20%) tan solid; $^1$H NMR CDCl$_3$: 1.88-1.99 (m, 4H), 3.22-3.25 (m, 2H), 3.90 (m, 2H), 5.76 (bs, 1H) 6.95 (m, 1H), 7.10 (m, 2H).

c) 3-(4-methoxyphenyl)-6,7,8,9-tetrahydro-5H-[1,2,4]triazolo[4,3-a][1,3]diazepine 300 mg (34%) white solid; $^1$H NMR CDCl$_3$: 2.03 (m, 4H), 3.48 (m, 4H), 5.33 (s, 3H), 6.96 (d, 2H), 7.87 (d, 2H).

EXAMPLE 6

3-(trifluoromethyl)-6,7,8,9-tetrahydro-5H-[1,2,4]triazolo[4,3-a][1,3]diazepine

Trifluoroacetic acid anhydride (0.24 ml, 1.71 mmol) was added to a solution of 1,3-diazepan-2-one hydrazone hydroiodide in DCM (10 ml). The reaction mixture was stirred for 24 h at r.t. The volatiles were removed and the residue was refluxed in aq. sat. NaHCO$_3$ for 2 h. After cooling to r.t. the product was collected by filtration, washed with water and dried to afford 101 mg (31%) of the title compound.
$^1$H NMR: 1.85-1.96 (m, 4H), 3.17 (m, 2H), 3.99 (m, 2H), 5.04 (s, 1H).

EXAMPLE 7

1,3-diazepan-2-one hydrazone hydroiodide

Hydrazine hydrate (0.44 ml, 7.23 mmol) was added to a solution of 2-(methylthio)-4,5,6,7-tetrahydro-1H-1,3-diazepine hydroiodide (1.79 d, 6.58 mmol) in EtOH (12 ml). The reaction mixture was refluxed for 5 h and cooled to r.t. Et$_2$O was added and the product was collected by filtration, washed with Et$_2$O and dried under vacuum to give 1.46 g (100%) crude title compound which was used directly in the next step.

EXAMPLE 8

2-(methylthio)-4,5,6,7-tetrahydro-1H-1,3-diazepine

Methyl iodide (0.55 ml, 1.15 mmol) was added to a solution of 1,3-diazepane-2-thione (1.00 g, 7.68 mmol) in acetone (8 ml). The reaction mixture was refluxed for 15 min. EtOH was added to the hot solution to dissolve the solids. After cooling to r.t. hex. was added and the precipitate was collected by filtration, washed with hex. and dried to give 1.79 g (86%) crude title compound which was used directly in the next step.

EXAMPLE 9

3-pyridin-4-yl-6,7-dihydro-5H-pyrrolo[2,1-c][1,2,4]triazole

Me$_3$OBF$_4$ (2.66 g, 18 mmol) was added to a solution of 2-pyrollidinone in DCM (150 ml) and the reaction mixture was stirred for 24 h. The reaction mixture was washed with aq. sat. NaHCO$_3$, dried and concentrated. The residue was dissolved in EtOH (4 ml) and isonicotinic hydrazide (1.37 g, 10 mmol) was added. The mixture was heated in a microwave reactor for 1 h at 120° C. The volatiles were removed and the crude product purified with column chromatography (DCM/MeOH 20:1) to give 319 mg (11%) of the title compound. $^1$H NMR: 2.87 (m, 2H), 3.05 (t, 2H), 4.28 (t, 2H), 7.72 (d,2H), 8.72 (d, 2H).

EXAMPLE 10

3-(Chloromethyl)-5-(3-chloro-phenyl)-1,2,4-oxadiazole

Step A. The acyclic intermediate was obtained from 3-chlorobenzoic acid (2.82 g, 18 mmol), EDCl (3.46 g, 18 mmol), HOBt (2.76 g, 18 mmol) and 2-chloro-N-hydroxyacetamidine (1.75 g, 16.2 mmol) [Chem. Ber. 1907, 40, 1639] in DMF (40 mL). Step B: The cyclic compound was obtained from heating in DMF (40 mL) and purified by SPE chromatography on silica gel using 2% acetone in hex.s yielded the title compound (1.46 g, 39% yield over 2 steps). $^1$H NMR: 8.17 (m, 1H), 8.07 (dd, 1H), 7.60 (m, 1H), 7.55 (t, 1H), 4.69 (s, 2H).

EXAMPLE 11

3-(Bromomethyl)-5-(3-chlorophenyl)-1,2,4-oxadiazole 3-(chloromethyl)-5-(3-chlorophenyl)-1,2,4-oxadiazole (1.38 g, 6.0 mmol) and LiBr (0.90 g, 10.3 mmol) in THF (50 ml) was heated to reflux under a nitrogen atmosphere o.n. After cooling to r.t. EA was added and the organic phase was washed with $H_2O$ and brine, dried and evaporated to give the title compound (1.40 g, 85%). MS ($M^+$+1) 275

EXAMPLE 12

3-(1-chloroethyl)-5-(3-chlorophenyl)-1,2,4-oxadiazole 5 drops of DMF was added to 1-[5-(3-chlorophenyl)-1,2,4-oxadiazol-3-yl]ethanol (12.3 g, 54.9 mmol) in $SOCl_2$ (150 mL) and the reaction was heated at 70° C. for 5 h. The excess $SOCl_2$ was evaporated and the residue was purified by column chromatography (Hep to Hep-EA 5:1) to give 12.4 g (93%) of the title compound. $^1$H NMR: 1.96 (d, 3H) 5.20 (q, 1H) 7.46 (t, 1H) 7.59 (m, 1H) 8.04 (m, 1H) 8.17 (t, 1H)

EXAMPLE 13

1-[5-(3-chlorophenyl)-1,2,4-oxadiazol-3-yl]ethyl methanesulfonate

Methane sulfonyl chloride (40 µl, 0.49 mmol) was added to a mixture of TEA (95 µl, 0.67 mmol) and 1-[5-(3-chlorophenyl)-1,2,4-oxadiazol-3-yl]ethanol (100 mg, 0.45 mmol) in DCM (5 ml). After stirring for 15 min the mixture was washed with water and brine, dried and concentrated and the title compound was obtained in 135 mg yield. $^1$H NMR: 1.9 (d, 3H), 3.1 (s, 3H), 5.9 (q, 1H), 7.5 (t, 1H), 7.6 (m, 1H), 8.0 (m, 1H), 8.1 (t, 1H)

EXAMPLE 14

1-[5-(3-chlorophenyl)-1,2,4-oxadiazol-3-yl]ethanol 27.2 g crude N'-[(3-chlorobenzoyl)oxy]-2-hydroxypropanimidamide was dissolved in ethanol (250 mL) and refluxed for 1 h, followed by addition of 14.0 g (170 mmol) sodium acetate in water (40 mL). After refluxing o.n., cooling to r.t. and addition of water (250 mL) the mixture was concentrated in vacuo to about ½ of its volume, resulting in a precipitate which was filtered off and recrystallized from EA/Hep to yield 6.45 g (25%) of the title compound. $^1$H NMR: 8.14 (s, 1H), 8.02 (d, 1H), 7.57 (d, 1H), 7.47 (t, 1H), 5.04 -5.14 (m, 1H), 2.51 (d, 1H), 1.67 (d, 3H)

EXAMPLE 15

N'-[(3-chlorobenzoyl)oxy]-2-hydroxypropanimidamide 6.45 g crude N',2-dihydroxypropanimidamide was cooled on an ice-bath with 23.5 mL DEA in THF (200 mL). To this slurry 21.94 g 3-chlorobenzoyl chloride was added. The mixture was warmed to r.t. and stirred for 2 h. Addition of $Et_2O$ (200 mL), washing with sat. aq. $NH_4Cl$ and re-extraction of the aq. layer gave after combining and concentration of the org. layers followed by drying in vacuo 27.24 g of crude title compound, which was directly used in the next step. LC-MS ($M^+$+1): 243.

EXAMPLE 16

N',2-dihydroxypropanimidamide 44.2 g (0.64 mol) of hydroxylamine hydrochloride and 25.5 g (0.64 mol) sodium hydroxide were dissolved in ethanol (500 mL) at r.t. and stirred for 3 h. After filtration, 8.11 g (0.11 mol) 2-hydroxypropanenitrile were added to the filtrate, followed by stirring for 4 h. After concentration to dryness the title compound was obtained which was directly used in the next step. $^1$H NMR (DMSO-D6): 8.88 (s, 1 H), 5.15 (s, 1H), 5.02 (s, 1H), 4.00 (q, 1H), 1.19 (d, 3H).

EXAMPLE 17

2-Ethoxycarbonylmethyl-3-oxo-piperazine-1-carboxylic acid tert-butyl ester

Triethyl amine (9.0 mL, 64.4 mmol) and di-tert-butyl-dicarbonate (7.0 g, 32.2 mmol) were added to (3-oxo-piperazin-2-yl)-acetic acid ethyl ester (4.0 g, 21.5 mmol) in 1,4-dioxane (4.0 mL) and water (2 mL) at room temperature and stirred overnight. The reaction mixture was concentrated and then the residue was diluted with dichloromethane. The organic layer was washed with water and brine, dried over anhydrous sodium sulfate, filtered and concentrated. The residue was triturated with hexanes, filtered, and dried to afford the titled compound (5.66 g, 92%, white solid).

$^1$H NMR ($CDCl_3$) δ (ppm): 6.29 (bs, 1H), 4.78 (m, 1H), 4.16 (m, 3H), 3.40 (m, 3H), 2.99 (m, 1H), 2.90 (m, 1H), 1.50 (s, 9H), 1.28 (t, 3H).

EXAMPLE 18

2-Carboxymethyl-3-oxo-piperazine-1-carboxylic acid tert-butyl ester

1N Sodium hydroxide (11.4 mL, 11.4 mmol) was added to 2-ethoxycarbonylmethyl-3-oxo-piperazine-1-carboxylic acid tert-butyl ester (2.5 g, 8.73 mmol) in methanol (20 mL) at room temperature and then stirred for 2.5 hours. The reaction mixture was concentrated, acidified with 2N HCl to pH~2 and extracted with dichloromethane (3 times). The organic layer was washed with brine, dried over anhydrous sodium sulfate, filtered and concentrated to afford the titled compound (1.87 g, 83%, white foam solid). $^1$H NMR ($CDCl_3$) δ (ppm): 7.68 (bs, 1H), 4.78 (m, 1H), 4.19 (m, 1H), 3.45 (m, 1H), 3.34 (m, 2H), 2.97 (m, 2H), 1.49 (s, 9H).

EXAMPLE 19

2-[3-(3-Chloro-phenyl)-[1,2,4]oxadiazol-5-yl]-3-oxo-piperazine-1-carboxylic acid tert-butyl ester 2-Carboxymethyl-3-oxo-piperazine-1-carboxylic acid tert-butyl ester (1.87 g, 7.25 mmol), 3-chloro-N-hydroxybenzamidine (1.36 g, 7.98 mmol), HOBt (1.08 g, 7.98 mmol) and EDCl (1.53 g, 7.98 mmol) in DMF (20 mL) were stirred at room temperature overnight. The reaction mixture was diluted with ethyl acetate, washed with water (3 times), saturated sodium bicarbonate (2 times) and brine, dried over anhydrous sodium sulfate, filtered and concentrated. The residue was dissolved in DMF (20 mL) and then heated at 135° C. for 4 hours. After cooling, the reaction mixture was diluted with ethyl acetate, washed with water (3 times) and brine, dried over anhydrous sodium sulfate, filtered and concentrated. Purification was performed by flash chromatography on silica gel using hexanes:dichloromethane (1:1) to afford the titled compound (1.48 g, 52%, white foam solid). $^1$H NMR ($CDCl_3$) δ (ppm): 8.08 (m, 1H), 7.97 (m, 1H), 7.46 (m, 2H), 6.35 (m, 1H), 5.04 (m, 1H), 4.31 (m, 1H), 3.68 (m,1H), 3.50 ( m, 2H), 3.27 (m, 2H), 1.35 (bs, 9H).

EXAMPLE 20

6-[3-(3-Chloro-phenyl)-[1,2,4]oxadiazol-5-yl]-5-methoxy-3,6-dihydro-2H-pyrazine-1-carboxylic acid tert-butyl ester Trimethyloxoniuim tetrafluoroborate (169.4 mg, 1.15 mmol) was added to 2-[3-(3-chloro-phenyl)-[1,2,4]oxadiazol-5-yl]-3-oxo-piperazine-1-carboxylic acid tert-butyl ester (450 mg, 1.15 mmol) in dichloromethane (3 mL) under argon at room temperature and then stirred overnight. The reaction mixture was directly purified by flash chromatography on basic alumina using 30% ethyl acetate in hexanes to afford the titled compound (284.6 mg, 61%). $^1$H NMR (CDCl$_3$) δ (ppm): 8.09 (m, 1H), 7.97 (m, 1H), 7.46 (m, 2H), 4.88 (m, 1H), 4.01 (m, 1H), 3.72 (s, 3H), 3.51 (m, 3H), 3.35 (m, 1H), 2.90 (m, 1H), 1.34 (m, 9H).

EXAMPLE 21

8-[3-(3-Chloro-phenyl)-[1,2,4]oxadiazol-5-yl]-3-(4-methoxy-phenyl)-5,6-dihydro-8H-[1,2,4]triazolo[4,3-a]pyrazine-7-carboxylic acid tert-butyl ester 6-[3-(3-Chloro-phenyl)-[1,2,4]oxadiazol-5-yl]-5-methoxy-3,6-dihydro-2H-pyrazine-1-carboxylic acid tert-butyl ester (284.6 mg, 0.70 mmol) and 4-methoxy-benzoic acid hydrazide (116.2 mg, 0.70 mmol) under argon in methanol (10 mL) were heated at reflux for 3 days. After cooling, the reaction mixture was diluted with ethyl acetate and then washed with water (3 times) and brine, dried over anhydrous sodium sulfate, filtered and concentrated. Purification by flash chromatography on silica gel using 40-85% ethyl acetate in hexanes afforded the titled compound (72.5 mg, 20%). $^1$H NMR (CDCl$_3$) δ (ppm): 8.07 (m, 1H), 7.96 (m, 1H), 7.64 (m, 2H), 7.47 (m, 2H), 7.05 (m, 2H), 6.04 (m, 1H), 4.11 (m, 2H), 3.89 (s, 3H), 3.86 (m, 2H), 3.55 (m, 1H), 3.31 (m, 1H), 1.28 (bs, 9H).

EXAMPLE 22

[5-(3-Chloro-phenyl)-isoxazol-3-yl]-methanol a) 4-(3-Chloro-phenyl)-2,4-dioxo-butyric acid ethyl ester

Sodium hydride (60% oil dispersion, 1.24 g, 31.1 mmol) was added in portions to a solution of 3-chloroacetophenone (4.0 g, 25.9 mmol) and diethyl oxalate (4.54 g, 31.1 mmol) in DMF (32 ml) at 0° C. The mixture stirred at room temperature for 1 h and was then heated at 80° C. for a half an h. After cooling, the mixture was treated with 3N HCl and then diluted with ethyl acetate. The organic layer was washed with water (3X) and saturated brine, dried over anhydrous sodium sulfate, filtered and concentrated. The resulting residue was then purified by flash column chromatography on silica using 0-10% ethyl acetate in hexanes to afford of 4-(3-chloro-phenyl)-2,4-dioxo-butyric acid ethyl ester (4.43 g, 67%, yellow solid). 1H NMR (CDCl$_3$) d (ppm): 15.12 (br s, 1H), 7.98 (s, 1H), 7.88 (d, 1H), 7.58 (d, 1H), 7.47 (t, 1H), 7.05 (s, 1H), 4.39 (m, 2H), 1.41 (m, 3H).

b) 5-(3-Chloro-phenyl)-isoxazole-3-carboxylic acid ethyl ester

A solution of 4-(3-chloro-phenyl)-2,4-dioxo-butyric acid ethyl ester (3.0 g, 11.8 mmol) and hydroxylamine hydrochloride (2.46 g, 35.4 mmol) in methanol (60 ml) was heated at 80° C. for 4 h. After cooling, the mixture was filtered and washed with cold methanol to afford 5-(3-chloro-phenyl)-isoxazole-3-carboxylic acid ethyl ester (2.0 g, 71%, white solid). 1H NMR (CDCl$_3$) d (ppm): 7.82 (s, 1H), 7.72 (m, 1H), 7.47 (m, 2H), 4.03 (s, 3H). Mixture of both methyl and ethyl ester (mostly methyl).

c) [5-(3-chloro-phenyl)-isoxazol-3-yl]-methanol

Lithium aluminum hydride (320 mg, 8.4 mmol) was slowly added to a solution of 5-(3-chloro-phenyl)-isoxazole-3-carboxylic acid ethyl ester (2.0 g, 8.4) in THF (100 mL) at room temperature. After 1 hour, the reaction mixture was quenched with water and then extracted with ethyl acetate. The organic layer was washed with water and saturated brine, dried over anhydrous sodium sulfate, filtered, and concentrated. The resulting residue was then purified by flash column chromatography using 15-40% ethyl acetate in hexane to afford [5-(3-chloro-phenyl)-isoxazol-3-yl]-methanol (1.32 g, 75%, yellow solid). $^1$H NMR (CDCl$_3$) δ (ppm): 7.78 (s, 1H), 7.68 (m, 1H), 7.43 (m, 2H), 6.63 (s, 1H), 4.84 (d, 2H), 2.23 (t, 1H).

EXAMPLE 23

Methanesulfonic acid 5-(3-chloro-phenyl)-isoxazol-3-ylmethyl ester

Triethyl amine (965 mg, 9.5 mmol) and methanesulfonyl chloride (820 mg, 7.2 mmol) were added to a solution of [5-(3-chloro-phenyl)-isoxazol-3-yl]-methanol (1.0 g, 4.8 mmol) in dichloromethane (50 mL) at 0° C. After 1 hour, the reaction mixture was quenched with cold saturated sodium bicarbonate and then the organic layer was washed with saturated brine, dried over anhydrous sodium sulfate, filtered, and concentrated to afford methanesulfonic acid 5-(3-chloro-phenyl)-isoxazol-3-ylmethyl ester (1.4 g, 100%, light brown solid). $^1$H NMR (CDCl$_3$) δ (ppm): 7.80 (s, 1H), 7.70 (m, 1H), 7.45 (m, 2H), 6.73 (s, 1H), 5.37 (s, 2H), 3.16 (s, 3H).

EXAMPLE 24

5-(5-Chloro-2-fluoro-phenyl)-3-chloromethyl-[1,2,4]oxadiazole

The acyclic intermediate was prepared from 2-fluoro-5-chlorobenzoic acid (550 mg, 3.15 mmol), EDCI (665 mg, 3.47 mmol), HOBT (469 mg, 3.47 mmol) and 2-chloro-N-hydroxy-acetamidine (377 mg, 3.47 mmol) in DMF (10 mL). To effect cyclization to oxadiazole, DMF (15 mL) was added to the intermediate residue and the mixture was heated for 1 hour. The product was purified by flash column chromatography using 10% ethyl acetate in hexane afforded the title compound (438 mg, 56% yield over 2 steps, white solid). 1H NMR (CDCl$_3$) δ (ppm): 8.16 (m, 1H), 7.58 (m, 1H), 7.29 (m, 1H), 4.72 (s, 3H).

Preparation of Final Compounds

EXAMPLE 25

7-[5-(5-Chloro-2-fluorophenyl)-1,2,4-oxadiazol-3-yl]-3-(2-thienyl)-6,7-dihydro-5H-[1,2,4]triazolo[3,4-b][1,3]thiazine To a solution of 2-[3-({[5-(5-chloro-2-fluorophenyl)-1,2,4-oxadiazol-3-yl]methyl}thio)-5-(2-thienyl)-4H-1,2,4-triazol-4-yl]ethyl methanesulfonate (43 mg) in DMF (2 ml) was added sodium hydride (10 mg) at −78° C. while stirring. The mixture was allowed to come to r.t. and stirred for another 3 h before addition of MeOH (1 ml) and concentration onto silica gel. Purification by chromatography on silica gel using DCM: EA:MeOH 70:30:2 as eluent provided 2.8 mg of the title compound. $^1$H NMR: 8.07 (dd, 1H), 7.56 (m, 1H), 7.51 (dd, 1H), 7.47 (dd, 1H), 7.17-7.23 (m, 2H), 4.86 (dd, 1H), 4.60 (m, 1H), 4.38 (m, 1H), 2.82 (m, 2H)

EXAMPLE 26 a) 9-{[5-(3-chlorophenyl)-1,2,4-oxadiazol-3-yl]methyl}-3-pyridin-4-yl-6,7,8,9-tetrahydro-5H-[1,2,4]triazolo[4,3-a][1,3]diazepine NaH (65 mg, 0.28 mmol) was added to a solution of 3-pyridin-4-yl-6,7,8,9-tetrahydro-5H-[1,2,4]triazolo[4,3-a][1,3]diazepine (54 mg, 0.25 mmol) in DMF (5 ml). After 10 min 3-(chloromethyl)-5-(3-chlorophenyl)-1,2,4-oxadiazole (65 mg, 0.28 mmol) was added at r.t. Stirring was continued o.n. and NH$_4$Cl solution, sat., was added and the mixture was extracted with EA. The organic phase was dried and concentrated. Flash chromatography (DCM/MeOH 20:1) yielded 56 mg (54%) of the title compound. $^1$H NMR: 1.89-2.01 (m, 4H), 3.33-3.42 (m, 2H), 3.90-3.98 (m, 2H), 4.88 (s, 2H), 7.42-7.49 (m, 3H), 7.53 (m, 1H), 7.98 (m, 1H), 8.09 (m, 1H), 8.71 (d, 2H).

The following compounds were prepared in an analogous manner:

b) 9-{[5-(3-chlorophenyl)isoxazol-3-yl]methyl}-3-(3,5-difluorophenyl)-6,7,8,9-tetrahydro-5H-[1,2,4]triazolo[4,3-a][1,3]diazepine yield 31.8 mg (61%) yellow solid; $^1$H NMR CDCl$_3$: 7.95 (s, 1H), 7.68 (m, 1H), 7.41 (m, 2H), 7.13 (m, 2H), 6.95 (m, 2H), 4.77 (s, 2H), 3.91 (m, 2H), 3.22 (m, 2H), 1.93 (br, 4H)

c) 9-{[5-(3-chlorophenyl)isoxazol-3-yl]methyl}-3-(4-methoxyphenyl)-6,7,8,9-tetrahydro-5H-[1,2,4]triazolo[4,3-a][1,3]diazepine yield 17.2 mg (45%) yellow solid; $^1$H NMR CDCl$_3$: 7.52 (br, 1H), 7.49 (m, 1H), 7.41 (d, 2H), 7.28 (m, 2H), 7.01 (d, 2H), 4.77 (s, 2H), 3.89 (s, 4H), 3.2 (m, 2H), 2.32 (s, 2H), 2.01 (m, 4H)

d) 9-{[5-(3-chlorophenyl)isoxazol-3-yl]methyl}-3-pyridin-4-yl-6,7,8,9-tetrahydro-5H-[1,2,4]triazolo[4,3-a][1,3]diazepine 47.4 mg (65%) yellow solid; $^1$H NMR CDCl$_3$: 8.79 (br, 2H), 7.79 (m, 1H), 7.68 (d, 1H), 7.53 (m, 2H), 7.51 (d, 2H), 6.99 (s, 1H), 4.79 (s, 2H), 3.96 (m, 2H), 3.22 (s, 2H), 1.94 (m, 4H)

e) 9-{[5-(5-chloro-2-fluorophenyl)-1,2,4-oxadiazol-3-yl]methyl}-3-pyridin-4-yl-6,7,8,9-tetrahydro-5H-[1,2,4]triazolo[4,3-a][1,3]diazepine 28 mg (33%) white solid; $^1$H NMR CDCl$_3$: 1.90-2.01 (m, 4H), 3.37-3.41 (m, 2H), 3.95-3.998 (m, 2H), 4.94 (s, 2H), 7.22 (t, 1H), 7.49-7.59 (m, 3H), 8.11 (q, 1H), 8.76 (q, 2H).

f) 9-{[5-(3-chlorophenyl)-1,2,4-oxadiazol-3-yl]methyl}-3-(3,5-difluorophenyl)-6,7,8,9-tetrahydro-5H-[1,2,4]triazolo[4,3-a][1,3]diazepine 10 mg (10%) white solid; $^1$H NMR CDCl$_3$: 1.89-2.01 (m, 4H), 3.38-3.46 (m, 2H), 3.90-3.98 (m, 2H), 4.90 (s, 2 H), 6.85-6.95 (m, 1H) 7.08-7.15 (m, 2H), 7.49 (t, 1H), 7.58 (d, 1H), 8.03 (d, 1H), 8.14 (m, 1H).

g) 9-{[5-(3-chlorophenyl)-1,2,4-oxadiazol-3-yl]methyl}-3-(4-methoxyphenyl)-6,7,8,9-tetrahydro-5H-[1,2,4]triazolo[4,3-a][1,3]diazepine 8mg (6%) tan solid; $^1$H NMR CDCl$_3$: 1.64 (bs, 4H), 3.18 (m, 2H), 3.60 (m, 5 H), 4.56 (s, 2 H), 6.87 (d, 2H) 7.26 (d, 2H), 7.48 (m, 1H), 7.55 (m, 1H), 7.88 (m, 1H).

EXAMPLE 27

9-{1-[5-(3-chlorophenyl)-1,2,4-oxadiazol-3-yl]ethyl}-3-pyridin-4-yl-6,7,8,9-tetrahydro-5H-[1,2,4]triazolo[4,3-a][1,3]diazepine The title compound was prepared analogous to 9-{[5-(3-chlorophenyl)-1,2,4-oxadiazol-3-yl]methyl}-3-pyridin-4-yl-6,7,8,9-tetrahydro-5H-[1,2,4]triazolo[4,3-a][1,3]diazepine from 1-[5-(3-chlorophenyl)-1,2,4-oxadiazol-3-yl]ethyl methanesulfonate (186 mg, 0.61 mmol), 3-pyridin-4-yl-6,7,8,9-tetrahydro-5H-[1,2,4]triazolo[4,3-a][1,3]diazepine (200 mg, 0.56 mmol) to give 8.1 mg (4%) of the title compound. $^1$H NMR: 1.83 (d, 3H), 1.86-1.95 (m, 4H), 3.16-3.27 (m, 1H), 3.43-3.53 (m, 1H), 3.75-3.87 (m, 1H), 3.95-4.07 (m, 1H), 5.54 (q, 1H), 7.41-7.52 (m, 3H), 7.52-7.58 (m, 1H), 8.01 (m, 1H), 8.12 (m, 1H), 8.73 (m, 2H).

EXAMPLE 28

7-{[5-(3-chlorophenyl)-1,2,4-oxadiazol-3-yl]methyl}-3-pyridin-4-yl-6,7-dihydro-5H-pyrrolo[2,1-c][1,2,4]triazole nBuLi (2.5 M, hex., 600 µl) was added to a solution of 3-pyridin-4-yl-6,7-dihydro-5H-pyrrolo[2,1-c][1,2,4]triazole (250 mg, 1.33 mmol) in THF (13 ml) at 0° C. After 10 min the reaction mixture was cooled to −78° C. and 3-(bromomethyl)-5-(3-chlorophenyl)-1,2,4-oxadiazole (400 mg, 1.46 mmol) in THF (10 ml) was added. After stirring at −78° C. for 30 min stirring was continued at 0° C. reaching r.t. o.n. Aq. sat. NH$_4$Cl was added and the mixture was extracted with EA. The organic phase was washed with water and brine, dried and concentrated. Flash chromatography (DCM/MeOH 40:1) followed by preparative HPLC afforded 6.5 mg (1%) of the title compound. $^1$H NMR: 2.72 (m, 1H), 3.13 (m, 2H), 3.62 (m, 1H), 3.93 (m, 1H), 4.31 (m, 2H), 7.47 (t, 1H), 7.56 (m, 1H), 7.74 (d, 2H), 7.98 (m, 1H), 8.08 (m, 1H), 8.74 (m, 2H).

EXAMPLE 29

9-{[5-(3-chlorophenyl)-1,2,4-oxadiazol-3-yl]methyl}-3-(trifluoromethyl)-6,7,8,9-tetrahydro-5H-[1,2,4]triazolo[4,3-a][1,3]diazepine The title compound was prepared analogous to 9-{[5-(3-chlorophenyl)-1,2,4-oxadiazol-3-yl]methyl}-3-pyridin-4-yl-6,7,8,9-tetrahydro-5H-[1,2,4]triazolo[4,3-a][1,3]diazepine from 3-(chloromethyl)-5-(3-chlorophenyl)-1,2,4-oxadiazole (89 mg, 0.39 mmol), 3-(trifluoromethyl)-6,7,8,9-tetrahydro-5H-[1,2,4]triazolo[4,3-α][1,3]diazepine (73 mg, 0.35 mmol. Column chromatography (hep./EA 1:1) afforded 85 mg (61%) of the title compound. $^1$H NMR: 1.88 (m, 2H), 1.94 (m, 2H), 3.26-3.35 (m, 2H), 3.98-4.07 (m, 2H), 4.83 (s, 2H), 7.46 (m, 1H), 7.50-7.57 (m, 1H), 7.98 (m, 1H), 8.09 (m, 1H)

EXAMPLE 30

8-[3-(3-Chloro-phenyl)-[1,2,4]oxadiazol-5-yl]-3-(4-methoxy-phenyl)-5,6,7,8-tetrahydro-[1,2,4]triazolo[4,3-a]pyrazine Trifluoroacetic acid (0.5 mL) was added to a solution of 8-[3-(3-chloro-phenyl) -[1,2,4]oxadiazol-5-yl]-3-(4-methoxy-phenyl)-5,6-dihydro-8H-[1,2,4]triazolo[4,3-a]pyrazine-7-carboxylic acid tert-butyl ester (72.5 mg, 0.14 mmol) in dichloromethane (1 mL) at 0° C. The reaction mixture was then diluted with dichloromethane, After 15 minutes, the reaction was warmed to room temperature and stirred for an additional hour. washed with saturated sodium bicarbonate, dried over anhydrous sodium sulfate, filtered and concentrated. Purification was performed by flash column chromatography on silica gel using 85-90% ethyl acetate in hexanes to 2% ammonia in methanol in dichloromethane followed by trituration with diethyl ether to afford the titled compound (40.6 mg, 69%). $^1$H NMR (CDCl$_3$) δ (ppm): 8.10 (m, 1H), 8.00 (m, 1H), 7.67 (m, 2H), 7.48 (m, 2H), 7.05 (m, 2H), 7.86 (m, 1H), 4.09 (m, 3H), 3.89 (s, 3H), 3.47 (m, 2H), 3.24 (m, 1H), 2.83 (bs, 1H).

EXAMPLE 31

8-[3-(3-Chloro-phenyl)-[1,2,4]oxadiazol-5-yl]-3-(4-methoxy-phenyl)-7-methyl-5,6,7,8-tetrahydro-[1,2,4]triazolo[4,3-a]pyrazine Formic acid (0.1 mL), formaldehyde (37 wt. % solution in water, 0.1 mL) and sodium cyanoborohydride (1.0 M in THF, 0.1 mL) were added to a solution of 8-[3-(3-chloro-phenyl)-[1,2,4]oxadiazol-5-yl]-3-(4-methoxy-phenyl)-5,6,7,8-tetrahydro-[1,2,4]triazolo[4,3-a]pyrazine (30 mg, 0.071 mmol) in methanol (0.8 mL) at room temperature. After stirring for 30 minutes, the reaction mixture was diluted with water and then extracted with chloroform (4 times), dried over anhydrous sodium sulfate, filtered and concentrated. Purification by flash chromatography on silica gel; using 50% ethyl acetate in hexanes, ethyl acetate and 4% 2M ammonia in methanol in dichloromethane afforded the titled compound (23.8 mg, 77%). $^1$H NMR (CDCl$_3$) δ (ppm): 8.04 (m, 1H), 7.93 (m, 1H), 7.68 (m, 2H), 7.42 (m, 2H), 7.03 (m, 2H), 4.37 (m,1H), 4.07 (m, 2H), 3.89 (m, 3H), 3.82 (m, 2H), 3.11 (m, 1H), 2.88 (m, 1H), 2.56 s, 3H).

PHARMACOLOGY

The pharmacological properties of the compounds of the invention can be analyzed using standard assays for functional activity. Examples of glutamate receptor assays are well known in the art as described in for example Aramori et al., Neuron 8:757 (1992), Tanabe et al., Neuron 8:169 (1992), Miller et al., J. Neuroscience 15: 6103 (1995), Balazs, et al., J. Neurochemistry 69:151 (1997). The methodology described in these publications is incorporated herein by reference. Conveniently, the compounds of the invention can be studied by means of an assay that measures the mobilization of intracellular calcium, [Ca$^{2+}$]$_i$ in cells expressing mGluR5.

For FLIPR analysis, cells expressing human mGluR5d as described in WO97/05252 were seeded on collagen coated clear bottom 96-well plates with black sides and analysis of [Ca$^{2+}$]$_i$ mobilization was done 24 h after seeding.

FLIPR experiments were done using a laser setting of 0.800 W and a 0.4 second CCD camera shutter speed. Each FLIPR experiment was initiated with 160 μl of buffer present in each well of the cell plate. After each addition of the compound, the fluorescence signal was sampled 50 times at 1 second intervals followed by 3 samples at 5 second intervals. Responses were measured as the peak height of the response within the sample period.

EC$_{50}$ and IC$_{50}$ determinations were made from data obtained from 8-point concentration response curves (CRC) performed in duplicate. Agonist CRC were generated by scaling all responses to the maximal response observed for the plate. Antagonist block of the agonist challenge was normalized to the average response of the agonist challenge in 14 control wells on the same plate.

We have validated a secondary functional assay for mGluR5d as described in WO97/05252 based on Inositol Phosphate (IP$_3$) turnover. IP$_3$ accumulation is measured as an index of receptor mediated phospholipase C turnover. GHEK cells stably expressing the human mGluR5d receptors were incubated with [3H]myo-inositol overnight, washed three times in HEPES buffered saline and pre-incubated for 10 min with 10 mM LiCl. Compounds (agonists) were added and incubated for 30 min at 37° C. Antagonist activity was determined by pre-incubating test compounds for 15 min, then incubating in the presence of glutamate (80 μM) or DHPG (30 μM) for 30 min. Reactions were terminated by the addition of perchloric acid (5%). Samples were collected and neutralized, and inositol phosphates were separated using Gravity-Fed Ion-Exchange Columns.

A detailed protocol for testing the compounds of the invention is provided in the assay below.

Assay of Group I Receptor Antagonist Activity

For FLIPR analysis, cells expressing human mGluR5d as described in WO97/05252 were seeded on collagen coated clear bottom 96-well plates with black sides and analysis of [Ca$^{2+}$]$_i$ mobilization was performed 24 h following seeding. Cell cultures in the 96-well plates were loaded with a 4 μM solution of acetoxymethyl ester form of the fluorescent calcium indicator fluo-3 (Molecular Probes, Eugene, Oreg.) in 0.01% pluronic. All assays were performed in a buffer containing 127 mM NaCl, 5 mM KCl, 2 mM MgCl$_2$, 0.7 mM NaH$_2$PO$_4$, 2 mM CaCl$_2$, 0.422 mg/ml NaHCO$_3$, 2.4 mg/ml HEPES, 1.8 mg/ml glucose and 1 mg/ml BSA Fraction IV (pH 7.4). FLIPR experiments were done using a laser setting of 0.800 W and a 0.4 second CCD camera shutter speed with excitation and emission wavelengths of 488 nm and 562 nm, respectively. Each FLIPR experiment was initiated with 160 μl of buffer present in each well of the cell plate. A 40 μl addition from the antagonist plate was followed by a 50 μL addition from the agonist plate. After each addition the fluorescence signal was sampled 50 times at 1 second intervals followed by 3 samples at 5 second intervals. Responses were measured as the peak height of the response within the sample period.

EC$_{50}$/IC$_{50}$ determinations were made from data obtained from 8 points concentration response curves (CRC) performed in duplicate. Agonist CRC were generated by scaling all responses to the maximal response observed for the plate. Antagonist block of the- agonist challenge was normalized to the average response of the agonist challenge in 14 control wells on the same plate.

Measurement of Inositol Phosphate Turnover in Intact Whole Cells

GHEK stably expressing the human mGluR5d receptor were seeded onto 24 well poly-L-lysine coated plates at $40 \times 10^4$ cells /well in media containing 1 μCi/well [3H]myo-inositol. Cells were incubated overnight (16 h), then washed three times and incubated for 1 h at 37° C. in HEPES buffered saline (146 mM NaCl, 4.2 mM KCl, 0.5 mM $MgCl_2$, 0.1% glucose, 20 mM HEPES, pH 7.4) supplemented with 1 unit/ml glutamate pyruvate transaminase and 2 mM pyruvate. Cells were washed once in HEPES buffered saline and pre-incubated for 10 min in HEPES buffered saline containing 10 mM LiCl. Compounds (agonists) were added and incubated at 37° C. for 30 min. Antagonist activity was determined by pre-incubating test compounds for 15 min, then incubating in the presence of glutamate (80 μM) or DHPG (30 μM) for 30 min. The reaction was terminated by the addition of 0.5 ml perchloric acid (5%) on ice, with incubation at 4° C. for at least 30 min. Samples were collected in 15 ml Falcon tubes and inositol phosphates were separated using Dowex columns, as described below.

Assay for Inositol Phosphates Using Gravity-Fed Ion-Exchange Columns

Preparation of Ion-Exchange Columns

Ion-exchange resin (Dowex AG1-X8 formate form, 200-400 mesh, BIORAD) was washed three times with distilled water and stored at 4° C. 1.6 ml resin was added to each column, and washed with 3 ml 2.5 mM HEPES, 0.5 mM EDTA, pH 7.4.

a) Sample Treatment

Samples were collected in 15 ml Falcon tubes and neutralized with 0.375 M HEPES, 0.75 M KOH. 4 ml of HEPES/EDTA (2.5/0.5 mM, pH 7.4) were added to precipitate the potassium perchlorate. Supernatant was added to the prepared Dowex columns.

b) Inositol Phosphate Separation

Elute glycero phosphatidyl inositols with 8 ml 30 mM ammonium formate. Elute total inositol phosphates with 8 ml 700 mM ammonium formate/100 mM formic acid and collect eluate in scintillation vials. Count eluate mixed with 8 ml scintillant.

One aspect of the invention relates to a method for inhibiting activation of mGluR 5, comprising treating a cell containing said receptor with an effective amount of the compound of formula I.

Screening for Compounds Active Against tlesr

Adult Labrador retrievers of both genders, trained to stand in a Pavlov sling, are used. Mucosa-to-skin esophagostomies are formed and the dogs are allowed to recover completely before any experiments are done.

Motility Measurement

In brief, after fasting for approximately 17 h with free supply of water, a multilumen sleeve/sidehole assembly (Dentsleeve, Adelaide, South Australia) is introduced through the esophagostomy to measure gastric, lower esophageal sphincter (LES) and esophageal pressures. The assembly is perfused with water using a low-compliance manometric perfusion pump (Dentsleeve, Adelaide, South Australia). An air-perfused tube is passed in the oral direction to measure swallows, and an antimony electrode monitored pH, 3 cm above the LES. All signals are amplified and acquired on a personal computer at 10 Hz.

When a baseline measurement free from fasting gastric/LES phase III motor activity has been obtained, placebo (0.9% NaCl) or test compound is administered intravenously (i.v., 0.5 ml/kg) in a foreleg vein. Ten min after i.v. administration, a nutrient meal (10% peptone, 5% D-glucose, 5% Intralipid, pH 3.0) is infused into the stomach through the central lumen of the assembly at 100 ml/min to a final volume of 30 ml/kg. The infusion of the nutrient meal is followed by air infusion at a rate of 500 ml/min until an intragastric pressure of 10±1 mmHg is obtained. The pressure is then maintained at this level throughout the experiment using the infusion pump for further air infusion or for venting air from the stomach. The experimental time from start of nutrient infusion to end of air insufflation is 45 min. The procedure has been validated as a reliable means of triggering TLESRs.

TLESRs is defined as a decrease in lower esophageal sphincter pressure (with reference to intragastric pressure) at a rate of >1 mmHg/s. The relaxation should not be preceded by a pharyngeal signal <2s before its onset in which case the relaxation is classified as swallow-induced. The pressure difference between the LES and the stomach should be less than 2 mmHg, and the duration of the complete relaxation longer than 1 s.

ABBREVIATIONS atm atmosphere
Aq aqueous
BOC tert-butoxycarbonyl
BSA Bovine Serum Albumin
nBu normal butyl
CCD Charge Coupled Device
MCPBA meta-chloroperoxybenzoic acid
CRC Concentration Response Curve
DCM dichloromethane
DEAD diethyl azodicarboxylate
DHPG 3,5-dihydroxyphenylglycine
DMAP 4(N,N-dimethylamino)pyridine
DMF N,N-dimethylformamide
EA ethyl acetate
EDC 1-Ethyl-3-(3-dimethylaminopropyl)carbodiimide
EDTA Ethylene Diamine Tetraacetic Acid
FLIPR Fluorometric Imaging Plate reader
GHEK GLAST-containing Human Embryonic Kidney
GLAST glutamate/aspartate transporter
h. hour
HBTU O-benzotriazol-1-yl-N,N,N',N'-tetramethyluronium hexafluorophosphate
HEPES 4-(2-hydroxyethyl)-1-piperazineethanesulfonic acid (buffer)
hep heptane
hex hexane(s)
$IP_3$ inositol triphosphate
LAH lithium aluminumhydride
Novozyme 435® Polymer supported *Candida Antartica* Lipase (Novozymes, Bagsvaerd, Denmark)
o.n. overnight
PCC Pyridinium chlorochromate
PPTS pyridinium p-toluenesulfonate
prep preparative
r.t. room temperature
sat. saturated
TBAF tetrabutylammonium fluoride
THF tetrahydrofuran
pTsOHp-toluenesulfonic acid

RESULTS

Typical $IC_{50}$ values as measured in the assays described above are 10 μM or less. In one aspect of the invention the $IC_{50}$ is below 2 μM. In another aspect of the invention the $IC_{50}$ is below 0.2 μM. In a further aspect of the invention the $IC_{50}$ is below 0.05 μM.

Examples of $IC_{50}$ values for individual compounds are given below:

| Compound | FLIPR $IC_{50}$ |
|---|---|
| 7-{[5-(3-chlorophenyl)-1,2,4-oxadiazole-3-yl]methyl}-3-pyridin-4-yl-6,7-dihydro-5H-pyrrolo[2,1-c][1,2,4]triazole | 49 nM |
| 9-{[5-(3-chlorophenyl)-1,2,4-oxadiazole-3-yl]ethyl}-3-pyridin-4-yl-6,7,8,9-tetrahydro-5H-[1,2,4]triazolo[4,3-a][1,3]diazepine | 81 nM |

The invention claimed is:
1. A compound of formula I:

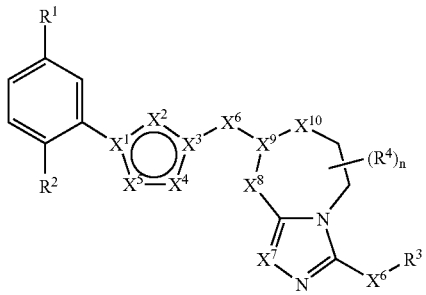

(I)

wherein
$X^1$, $X^2$, $X^3$, $X^4$, and $X^5$ are independently selected from the group consisting of C, $CR^5$, N, O, and S, wherein at least one of $X^1$, $X^2$, $X^3$, $X^4$, and $X^5$ is not N;
$X^6$ is selected from the group consisting of a bond and $CR^5R^6$;
$X^7$ is N;
$X^8$ is a bond;
$X^9$ is N;
$X^{10}$ is $(CR^5R^6)_2$;
$R^1$ is selected from the group consisting of hydroxy, halo, nitro, $C_{1-6}$alkylhalo, $OC_{1-6}$alkylhalo, $C_{1-6}$alkyl, $OC_{1-6}$alkyl, $C_{2-6}$alkenyl, $OC_{2-6}$alkenyl, $C_{2-6}$alkynyl, $OC_{2-6}$alkynyl, $C_{0-6}$alkyl$C_{3-6}$cycloalkyl, $OC_{0-6}$alkyl$C_{3-6}$cycloalkyl, $C_{0-6}$alkylaryl, $OC_{0-6}$alkylaryl, CHO, (CO)$R^5$, O(CO)$R^5$, O(CO)$OR^5$, $C_{1-6}$alkyl$OR^5$, $OC_{2-6}$alkyl$OR^5$, $C_{1-6}$alkyl(CO)$R^5$, $OC_{1-6}$alkyl(CO)$R^5$, $CO_{0-6}$alkyl$CO_2R^5$, $OC_{1-6}$alkyl$CO_2R^5$, $C_{0-6}$alkylcyano, $OC_{2-6}$alkylcyano, $C_{0-6}$alkyl$NR^5R^6$, $OC_{2-6}$alkyl$NR^5R^6$, $C_{1-6}$alkyl(CO)$NR^5R^6$, $OC_{1-6}$alkyl(CO)$NR^5R^6$, $C_{0-6}$alkyl$NR^5$(CO)$R^6$, $OC_{2-6}$alkyl$NR^5$(CO)$R^6$, $C_{0-6}$alkyl$NR^5$(CO)$NR^5R^6$, $C_{0-6}$alkyl$SR^5$, $OC_{2-6}$alkyl$SR^5$, $C_{0-6}$alkyl(SO)$R^5$, $OC_{2-6}$alkyl(SO)$R^5$, $C_{0-6}$alkyl$SO_2R^5$, $OC_{2-6}$alkyl$SO_2R^5$, $C_{0-6}$alkyl(SO$_2$)$NR^5R^6$, $OC_{2-6}$alkyl(SO$_2$)$NR^5R^6$, $C_{0-6}$alkyl$NR^5$(SO$_2$)$R^6$, $OC_{2-6}$alkyNR^5$(SO$_2$)$R^6$, $C_{0-6}$alkyl$NR^5$(SO$_2$)$NR^5R^6$, $OC_{2-6}$alkyl$NR^5$(SO$_2$)$NR^5R^6$, (CO)$NR^5R^6$, O(CO)$NR^5R^6$, $NR^5OR^6$, $C_{0-6}$alkyl$NR^5$(CO)$OR^6$, $OC_{2-6}$alkyl$NR^5$(CO)$OR^6$, $SO_3R^5$ and a 5- or 6-membered ring containing atoms independently selected from the group consisting of C, N, O and S, wherein said ring may be substituted by one or more A;
$R^2$ is selected from the group consisting of hydrogen, hydroxy, halo, nitro, $C_{1-6}$alkylhalo, $OC_{1-6}$alkylhalo, $C_{1-6}$alkyl, $OC_{1-6}$, $C_{2-6}$alkenyl, $OC_{2-6}$alkenyl, $C_{2-6}$alkynyl, $OC_{2-6}$alkynyl, $C_{0-6}$alkyl$C_{3-6}$cycloalkyl, $OC_{0-6}$alkyl$C_{3-6}$cycloalkyl, $C_{0-6}$alkylaryl, $OC_{0-6}$alkylaryl, CHO, (CO)$R^5$, O(CO)$R^5$, O(CO)$OR^5$, $C_{1-6}$alkyl$OR^5$, $OC_{2-6}$alkyl$OR^5$, $C_{1-6}$alkyl(CO)$R^5$, $OC_{1-6}$alkyl(CO)$R^5$, $C_{0-6}$alkyl$CO_2R^5$, $OC_{1-6}$alkyl$CO_2R^5$, $C_{0-6}$alkylcyano, $OC_{2-6}$alkylcyano, $C_{0-6}$alkyl$NR^5R^6$, $OC_{2-6}$alkyl$NR^5R^6$, $C_{1-6}$alkyl(CO)$NR^5R^6$, $OC_{1-6}$alkyl(CO)$NR^5R^6$, $C_{0-6}$alkyl$NR^5$(CO)$R^6$, $OC_{2-6}$alkyl$NR^5$(CO)$R^6$, $C_{0-6}$alkyl$NR^5$(CO)$NR^5R^6$, $C_{0-6}$alkyl$SR^5$, $OC_{2-6}$alkyl$SR^5$, $C_{0-6}$alkyl(SO)$R^5$, $OC_{2-6}$alkyl(SO)$R^5$, $C_{0-6}$alkyl$SO_2R^5$, $OC_{2-6}$alkyl$SO_2R^5$, $C_{0-6}$alkyl(SO$_2$)$NR^5R^6$, $OC_{2-6}$alkyl(SO$_2$)$NR^5R^6$, $C_{0-6}$alkyl$NR^5$(SO$_2$)$R^6$, $OC_{2-6}$alkyl$NR^5$(SO$_2$)$R^6$, $C_{0-6}$alkyl$NR^5$(SO$_2$)$NR^5R^6$, $OC_{2-6}$alkyl$NR^5$(SO$_2$)$NR^5R^6$, (CO)$NR^5R^6$, O(CO)$NR^5R^6$, $NR^5OR^6$, $C_{0-6}$alkyl$NR^5$(CO)$OR^6$, $OC_{2-6}$alkyl$NR^5$(CO)$OR^6$, $SO_3R^5$ and a 5- or 6-membered ring containing atoms independently selected from the group consisting of C, N, O and S, wherein said ring may be substituted by one or more A;
$R^3$ is a 5- or 6-membered ring containing atoms independently selected from the group consisting of C, N, O and S, wherein said ring may be substituted by one or more A;
$R^4$ is selected from the group consisting of hydroxy, halo, nitro, $C_{1-6}$alkylhalo, $OC_{1-6}$alkylhalo, $C_{1-6}$alkyl, $OC_{1-6}$alkyl, $C_{2-6}$alkenyl, $OC_{2-6}$alkenyl, $C_{2-6}$alkynyl, $OC_{2-6}$alkynyl, $OC_{2-6}$alkyl $C_{0-6}$alkyl$C_{3-6}$cycloalkyl, $OC_{0-6}$alkyl$C_{3-6}$cycloalkyl, $C_{0-6}$alkylaryl, $OC_{0-6}$alkylaryl, CHO, (CO)$R^5$, O(CO)$R^5$, O(CO)$OR^5$, $C_{1-6}$alkyl$OR^5$, $OC_{2-6}$alkyl$OR^5$, $C_{1-6}$alkyl(CO)$R^5$, $OC_{1-6}$alkyl($C_0$)$R^5$, $C_{0-6}$alkyl$CO_2R^5$, $OC_{1-6}$alkyl$CO_2R^5$, $C_{0-6}$alkylcyano, $OC_{2-6}$alkylcyano, $C_{0-6}$alkyl$NR^5R^6$, $OC_{2-6}$alkyl$NR^5R^6$, $C_{1-6}$alkyl(CO)$NR^5R^6$, $OC_{1-6}$alkyl(CO)$NR^5R^6$, $C_{0-6}$alkyl$NR^5$(CO)$R^6$, $OC_{2-6}$alkyl$NR^5$(CO)$R^6$, $C_{0-6}$alkyl$NR^5$(CO)$NR^5R^6$, $C_{0-6}$alkyl$SR^5$, $OC_{2-6}$alkyl$SR^5$, $C_{0-6}$alkyl(SO)$R^5$, $OC_{2-6}$alkyl(SO)$R^5$, $C_{0-6}$alkyl$SO_2R^5$, $OC_{2-6}$alkyl$SO_2R^5$, $C_{0-6}$alkyl(SO$_2$)$NR^5R^6$, $OC_{2-6}$alkyl(SO$_2$)$NR^5R^6$, $C_{0-6}$alkyl$NR^5$(SO$_2$)$R^6$, $OC_{2-6}$alkyl$NR^5$(SO$_2$)$R^6$, $C_{0-6}$alkyl$NR^5$(SO$_2$)$NR^5R^6$, $OC_{2-6}$alkyl$NR^5$(SO$_2$)$NR^5R^6$, (CO)$NR^5R^6$, O(CO)$NR^5R^6$, $NR^5OR^6$, $C_{0-6}$alkyl$NR^5$(CO)$OR^6$, $OC_{2-6}$alkyl$NR^5$(CO)$OR^6$, $SO_{03}R^5$ and a 5- or 6-membered ring containing atoms independently selected from the group consisting of C, N, O and S, wherein said ring may be substituted by one or more A;
$R^5$ and $R^6$ are independently selected from the group consisting of hydrogen, $C_{1-6}$alkyl, $C_{3-7}$cycloalkyl and aryl;
A is selected from the group consisting of hydrogen, hydroxy, halo, nitro, $C_{1-6}$alkylhalo, $OC_{1-6}$alkylhalo, $C_{1-6}$alkyl, $OC_{1-6}$alkyl, $C_{2-6}$alkenyl, $OC_{2-6}$alkenyl, $C_{2-6}$alkynyl, $OC_{2-6}$alkynyl, $C_{0-6}$alkyl$C_{3-6}$cycloalkyl, $OC_{0-6}$alkyl$C_{3-6}$cycloalkyl, $C_{0-6}$alkylaryl, $OC_{0-6}$alkyl aryl, CHO, (CO)$R^5$, O(CO)$R^5$, O(CO)$OR^5$, $C_{1-6}$alkyl $OR^5$, $OC_{2-6}$alkyl$OR^5$, $C_{1-6}$alkyl(CO)$R^5$, $OC_{1-6}$alkyl (CO)$R^5$, $C_{0-6}$alkyl$CO_2R^5$, $OC_{1-6}$alkyl$CO_2R^5$, $C_{0-6}$alkyl cyano, $OC_{2-6}$alkylcyano, $C_{0-6}$alkyl$NR^5R^6$, $C_{0-6}$alkyl$SR^5$, $OC_{2-6}$alkyl$SR^5$, $C_{0-6}$alkyl(SO)$R^5$, $OC_{2-6}$alkyl(SO)$R^5$, $C_{0-6}$alkyl$SO_2R^5$, $OC_{2-6}$alkyl$SO_2R^5$, $SO_3R^5$ and a 5- or 6-membered ring containing atoms independently selected from the group consisting of C, N, O and S;
n is 0, 1, 2, 3, or 4; or
a pharmaceutically acceptable salt or hydrate thereof;
provided that:
a) when $X^2=X^4=X^5=N$, and either of $X^8$ or $X^{10}$ is a bond, then $X^9$ is not N, b) when $X^7$ is N at least two of $X^1$, $X^2$, $X^3$, $X^4$, and $X^5$ are not N, c) $X^1$ and $X^3$ are not O.

2. The compound according to claim 1, wherein $R^1$ is halo, $C_{1-6}$alkylhalo, $C_{1-6}$alkyl, $OC_{1-6}$alkyl, or $C_{0-6}$alkylcyano.

3. The compound according to claim 1, wherein $R^2$ is hydrogen or halo.

4. The compound according to claim 1, wherein $R^2$ is fluorine.

5. The compound according to claim 1, of Formula II:

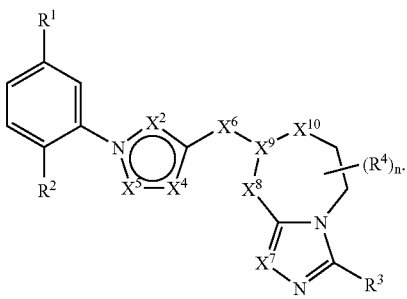

6. The compound according to claim 1, of Formula III:

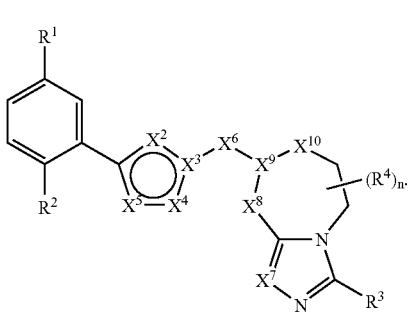

7. The compound according to claim 6, wherein $X^3$ is C.

8. The compound according to claim 6, wherein $X^3$ is N.

9. The compound according to claim 1, wherein the ring containing $X^1$, $X^2$, $X^3$, $X^4$, and $X^5$ is selected from the group consisting of:

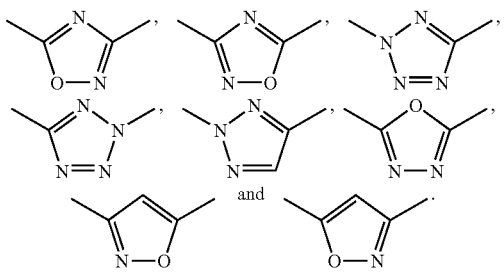

10. The compound according to claim 9, wherein the ring is selected from the group consisting of:

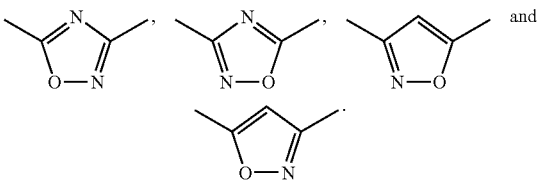

11. The compound according to claim 1 selected from the group consisting of:

9-{[5-(3-chlorophenyl)-1,2,4-oxadiazol-3-yl]methyl}-3-pyridin-4-yl-6,7,8,9-tetrahydro-5H-[1,2,4]triazolo[4,3-a][1,3]diazepine, 9-{1-[5-(3-chlorophenyl)-1,2,4-oxadiazol-3-yl]ethyl}-3-pyridin-4-yl-6,7,8,9-tetrahydro-5H-[1,2,4]triazolo[4,3-a][1,3]diazepine, 9-{[5-(3-chlorophenyl)isoxazol-3-yl]methyl}-3-(3,5-difluorophenyl)-6,7,8,9-tetrahydro-5H-[1,2,4]triazolo[4,3-a][1,3]diazepine, 9-{[5-(3-chlorophenyl)isoxazol-3-yl]methyl}-3-(4-methoxyphenyl)-6,7,8,9-tetrahydro-5H-[1,2,4]triazolo[4,3-a][1,3]diazepine, 9-{[5-(3-chlorophenyl)isoxazol-3-yl]methyl}-3-pyridin-4-6,7,8,9-tetrahydro-5H-[1,2,4]triazolo[4,3-a][1,3]diazepine, 9- {[5 -(5-chloro-2-fluorophenyl)-1,2,4-oxadiazol-3-yl]methyl }-3 -pyridin-4-yl-6,7, 8 ,9-tetrahydro-5H-[1,2,4]triazolo[4,3-a][1 ,3]diazepine, 9-{[5-(3-chlorophenyl)-1,2,4-isoxazol-3-yl]methyl}-3-(3,5-difluorophenyl)-6,7,8,9-tetrahydro-5H-[1,2,4]triazolo[4,3-a][1,3]diazepine, 9-{[5-(3-chlorophenyl)-1,2,4-isoxazol-3-yl]methyl}-3-(4-difluorophenyl)-6,7,8,9-tetrahydro-5H-[1,2,4]triazolo[4,3-a][1,3]diazepine, and pharmaceutically acceptable salts thereof.

12. A pharmaceutical composition comprising as active ingredient a therapeutically effective amount of the compound according to claim 1, and one or more pharmaceutically acceptable diluents, excipients, and/or inert carriers.

13. A method for the treatment of a psychiatric disorder comprising administering to a mammal in need thereof a therapeutically effective amount of the compound according to claim 1.

14. A method for the treatment of chronic and acute pain disorders comprising administering to a mammal in need thereof a therapeutically effective amount of the compound according to claim 1.

15. A method for the treatment of gastro-esophageal reflux disorder (GERD) comprising administering to a mammal in need thereof a therapeutically effective amount of the compound according to claim 1.

16. The method according to any one of claims 13, 14 and 15, wherein the mammal is a human.

\* \* \* \* \*